United States Patent [19]
Kitano et al.

[11] Patent Number: 5,814,654
[45] Date of Patent: Sep. 29, 1998

[54] SUBSTITUTED GUANIDINE DERIVATIVES

[75] Inventors: Masahumi Kitano, Takatsuki; Kazuhiro Nakano, Nishinomiya; Naohito Ohashi, Takatsuki, all of Japan

[73] Assignee: Sumitomo Pharmaceuticals Company, Limited, Osaka, Japan

[21] Appl. No.: 847,363

[22] Filed: Apr. 24, 1997

[30] Foreign Application Priority Data

Apr. 24, 1996 [JP] Japan .................................. 8-128973

[51] Int. Cl.$^6$ ........................ A61K 31/40; C07D 209/90
[52] U.S. Cl. ............................................. 514/411; 548/436
[58] Field of Search .............................. 548/436; 514/411

[56] References Cited

FOREIGN PATENT DOCUMENTS

| | | |
|---|---|---|
| A33014 | 8/1993 | Australia . |
| A33015 | 8/1993 | Australia . |
| A68844 | 2/1995 | Australia . |
| A81700 | 6/1995 | Australia . |
| A16354 | 10/1995 | Australia . |
| A17861 | 11/1995 | Australia . |
| A21720 | 1/1996 | Australia . |
| A30251 | 2/1996 | Australia . |
| A30144 | 3/1996 | Australia . |
| A30250 | 3/1996 | Australia . |
| 0604852 | 7/1994 | European Pat. Off. . |
| 0622356 | 11/1994 | European Pat. Off. . |
| 0676395 | 10/1995 | European Pat. Off. . |
| 0708091 | 4/1996 | European Pat. Off. . |
| 0719766 | 7/1996 | European Pat. Off. . |
| 0726254 | 8/1996 | European Pat. Off. . |
| WO9426709 | 11/1994 | WIPO . |

*Primary Examiner*—Mukund J. Shan
*Assistant Examiner*—Bruce Kifle
*Attorney, Agent, or Firm*—Sughrue, Mion, Zinn, Macpeak & Seas, PLLC

[57] ABSTRACT

A substituted guanidine derivative represented by the general formula:

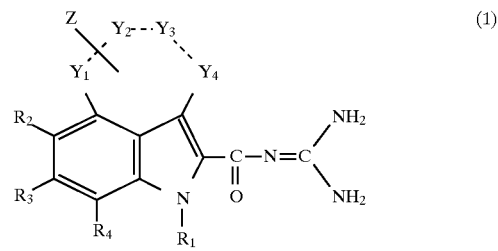

is useful as a therapeutic or prophylactic agent for diseases caused by the acceleration of the sodium/proton ($Na^+/H^+$) exchange transport system, for example, hypertension, arrhythmia, angina pectoris, cardiac hypertrophy, diabetes mellitus, organ disorders associated with ischemia or ischemic reperfusion, cerebroischemic disorders, diseases caused by excessive cell proliferation, or diseases caused by endothelial cell injury.

15 Claims, No Drawings

SUBSTITUTED GUANIDINE DERIVATIVES

BACKGROUND OF THE INVENTION

1. Field of the Invention

The present invention relates to novel substituted guanidine derivatives or salts thereof and a process for production thereof. The compounds of the present invention inhibit the sodium/proton ($Na^+/H^+$) exchange transport system and hence are useful as a therapeutic or prophylactic agent for diseases caused by the acceleration of the sodium/proton ($Na^+/H^+$) exchange transport system, for example, hypertension, arrhythmia, angina pectoris, cardiac hypertrophy, diabetes mellitus, organ disorders associated with ischemia or ischemic reperfusion [e.g. heart muscle ischemic reperfusion-associated disorders, acute renal failute, or disorders induced by surgical treatment such as organ transplantation or percutaneous transluminal coronary angioplasty (PTCA)], cerebro-ischemic disorders [e.g. disorders associated with cerebral infarction, disorders caused after cerebral apoplexy as sequelae, or cerebral edema], diseases caused by excessive cell proliferation such as proliferation of fibroblast, proliferation of smooth muscle cells or proliferation of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or recurrent stricture after PTCA, or diseases caused by endothelial cell injury.

2. Related Art Statement

As substituted guanidine derivatives having inhibitory effect on the sodium/proton ($Na^+/H^+$) exchange transport system, there are known, for example, pyrazinoylguanidine derivatives represented by amiloride (for instance, J. Membrane Biol., Vol. 105, 1 (1988); Circulation, Vol. 79, 1257 (1989)). It has been reported that benzoylguanidine derivatives inhibit the sodium/proton ($Na^+/H^+$) exchange transport system and hence have antiarrhythmic effect (for instance, J. Mol. Cell. Cardiol., Vol. 24, Suppl. I, S. 92 (1992); J. Mol. Cell. Cardiol., Vol. 24, Suppl. I, S. 117 (1992), Japanese Patent Unexamined Publication Nos. 5-339228, 6-9545, 6-345715 and 7-109251). It has also been reported that polycyclic aroylguanidine derivatives inhibit the sodium/proton ($Na^+/H^+$) exchange transport system (for instance, Japanese Patent Unexamined Publication Nos. 7-10839, 7-145149 and 7-206823).

SUMMARY OF THE INVENTION

The present invention is intended to provide novel substituted guanidine derivatives or salts thereof, which inhibit the sodium/proton ($Na^+/H^+$) exchange transport system and hence are useful as a therapeutic or prophylactic agent for diseases caused by the acceleration of the sodium/proton ($Na^+/H^+$) exchange transport system, for example, hypertension, arrhythmia, angina pectoris, cardiac hypertrophy, diabetes mellitus, organ disorders associated with ischemia or ischemic reperfusion [e.g. heart muscle ischemic reperfusion-associated disorders, acute renal failute, or disorders induced by surgical treatment such as organ transplantation or percutaneous transluminal coronary angioplasty (PTCA)], cerebro-ischemic disorders [e.g. disorders associated with cerebral infarction, disorders caused after cerebral apoplexy as sequelae, or cerebral edema], diseases caused by excessive cell proliferation such as proliferation of fibroblast, proliferation of smooth muscle cells or proliferation of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or recurrent stricture after PTCA, or diseases caused by endothelial cell injury;

a process for production of said derivatives or salts thereof; and medical use of said derivatives or salts thereof.

The present invention relates to substituted guanidine derivatives represented by the general formula (1):

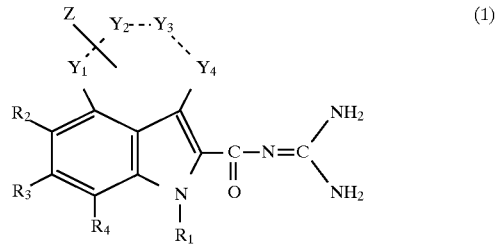

wherein $R_1$ is a hydrogen atom, an unsubstituted alkyl group, a substituted alkyl group, a cycloalkyl group, a cycloalkenyl group, a saturated heterocyclic group, an aromatic group, $-OR_5$, an acyl group or $-Q-R_a$;

$R_2$, $R_3$ and $R_4$ are independently a hydrogen atom, an unsubstituted alkyl group, a substituted alkyl group, a cycloalkyl group, a cycloalkenyl group, a saturated heterocyclic group, a halogen atom, a nitro group, a carboxyl group, an alkoxycarbonyl group, an aromatic group, $-OR_5$, $-N(R_6)R_7$, $-CON(R_6)R_7$, $-SO_2N(R_6)R_7$, $-S(O)nR_8$, an acyl group, $-Q-R_a$ or

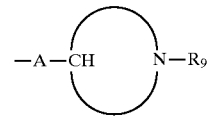

wherein the ring is a 3- to 8-membered saturated heterocyclic group composed of a nitrogen atom and carbon atoms;

$Y_1$, $Y_2$, $Y_3$ and $Y_4$ are as follows: ① one of them is a methylene group, a carbonyl group, an oxygen atom, $-S(O)_n-$, $-N(R_{10})-$ or $-C(=C(R_{11})(R_{12}))-$, two others are independently a methylene group, and the remaining one is a single bond or a methylene group, or ② any adjacent two members of a group consisting of $Y_1$, $Y_2$, $Y_3$ and $Y_4$ are taken together to represent a vinylene group ($-CH=CH-$) or $-CON(R_{10})-$, another is a methylene group, a carbonyl group, an oxygen atom, $-S(O)_n-$, $-N(R_{10})-$ or $-C(=C(R_{11})(R_{12}))-$, and the remaining one is a single bond or a methylene group, provided that the oxygen atom, nitrogen atom and sulfur atom are not directly bonded to the vinylene group;

Z is a substituent which may be substituted for at least one hydrogen atom (for example, one or two hydrogen atoms) bonded to any of the carbon atoms constituting the ring formed by $Y_1$, $Y_2$, $Y_3$ and $Y_4$, namely, Z may be absent, or one or more Zs may be present and are independently a substituent selected from the group consisting of unsubstituted alkyl groups, substituted alkyl groups, alkenyl groups, alkynyl groups, cycloalkyl groups, cycloalkenyl groups, saturated heterocyclic groups, halogen atoms, carboxyl group, alkoxycarbonyl groups, aromatic groups, $-OR_5$, $-N(R_6)R_7$, $-CON(R_6)R_7$, $-S(O)_nR_8$, acyl groups and $-Q-R_a$;

A is an oxygen atom, —S(O)$_n$— or —N(R$_{10}$)—;

Q is a substituted or unsubstituted lower alkylene group;

R$_a$ is a substituted or unsubstituted vinyl group, or a substituted or unsubstituted ethynyl group;

R$_5$ is a hydrogen atom, an unsubstituted alkyl group, a substituted alkyl group, a cycloalkyl group, a cycloalkenyl group, a saturated heterocyclic group or an aromatic group;

R$_6$ and R$_7$ are independently a hydrogen atom, an unsubstituted alkyl group, a substituted alkyl group, a cycloalkyl group, a cycloalkenyl group, a saturated heterocyclic group, an aromatic group, an acyl group or —Q—R$_a$, or R$_6$ and R$_7$, when taken together with the nitrogen atom to which they are bonded, form a saturated 5- to 7-membered cyclic amino group which may contain an oxygen atom or a sulfur atom in the ring and may be substituted by one or more (for example, two) unsubstituted alkyl groups, substituted alkyl groups, hydroxyl groups or —OR$_5$ groups;

R$_8$ is an unsubstituted alkyl group, a substituted alkyl group or an aromatic group;

R$_9$ is a hydrogen atom, an unsubstituted alkyl group, a substituted alkyl group, an acyl group or —Q—R$_a$;

R$_{10}$ is a hydrogen atom, an unsubstituted alkyl group, a substituted alkyl group, a cycloalkyl group, a saturated heterocyclic group, an aromatic group, an acyl group or —Q—R$_a$;

R$_{11}$ and R$_{12}$ are independently a hydrogen atom, an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, —OR$_5$, —N(R$_6$)R$_7$, —CON(R$_6$)R$_7$, —S(O)$_n$R$_8$, an acyl group or —Q—R$_a$; and n is 0, 1 or 2, or pharmaceutically acceptable acid addition salts thereof, a process for production of said derivatives or salts thereof, and medical use of the derivatives or salts.

DETAILED DESCRIPTION OF THE INVENTION

The various groups in the present invention are explained below.

The alkyl group includes, for example, linear or branched alkyl groups of 8 or less carbon atoms, such as methyl, ethyl, propyl, 2-propyl, butyl, 2-butyl, 2-methylpropyl, 1,1-dimethylethyl, pentyl, hexyl, heptyl, octyl, etc.

The cycloalkyl group may be unsubstituted or may be substituted by 1 to 4 unsubstituted alkyl groups, substituted alkyl groups, hydroxyl groups or groups of the formula —OR$_5$, and includes, for example, 3- to 8-membered cycloalkyl groups such as cyclopropyl, cyclobutyl, cyclopentyl, cyclohexyl, cycloheptyl, 2-methylcyclopentyl, 3-methylcyclopentyl, 2-methylcyclohexyl, 3-methylcyclohexyl, 4-methylcyclohexyl, 2-hydroxycyclopentyl, 3-hydroxycyclopentyl, 2-hydroxycyclohexyl, 3-hydroxycyclohexyl, 4-hydroxycyclohexyl, 2-(hydroxymethyl)cyclopentyl, 3-(hydroxymethyl)cyclopentyl, 2-(hydroxymethyl)cyclohexyl, 3-(hydroxymethyl)cyclohexyl, 4-(hydroxymethyl)cyclohexyl, 2-(aminomethyl)cyclopentyl, 3-(aminomethyl)cyclopentyl, 2-(aminomethyl)cyclohexyl, 3-(aminomethyl)cyclohexyl, 4-(aminomethyl)cyclohexyl, 2-(methoxymethyl)cyclopentyl, 3-(methoxymethyl)cyclopentyl, 2-(methoxymethyl)cyclohexyl, 3-(methoxymethyl)cyclohexyl, 4-(methoxymethyl)cyclohexyl, etc.

The cycloalkenyl group may be unsubstituted or may be substituted by 1 to 4 unsubstituted alkyl groups, substituted alkyl groups, hydroxyl groups or groups of the formula —OR$_5$, and includes, for example, 3- to 8-membered cycloalkenyl groups having a double bond, such as 1-cyclopentenyl, 2-cyclopentenyl, 3-cyclopentenyl, 1-cyclohexenyl, 2-cyclohexenyl, 3-cyclohexenyl, etc.

The saturated heterocyclic group may be unsubstituted or may be substituted by 1 to 4 unsubstituted alkyl groups, substituted alkyl groups, hydroxyl groups or groups of the formula —OR$_5$, and includes, for example, 3- to 8-membered saturated heterocyclic groups having an oxygen atom or a sulfur atom, such as 2-tetrahydrofuranyl, 3-tetrahydrofuranyl, 2-tetrahydro-2H-pyranyl, 4-tetrahydro-4H-pyranyl, etc.

The halogen atom includes, for example, fluorine, chlorine and bromine atoms.

The alkoxycarbonyl group includes, for example, linear or branched alkoxycarbonyl group of 6 or less carbon atoms, such as methoxycarbonyl, ethoxycarbonyl, propoxycarbonyl, 2-propoxycarbonyl, etc.

The aromatic group includes substituted or unsubstituted aryl groups and substituted or unsubstituted heteroaryl groups. As the aryl groups, there may be exemplified aryl groups of 10 or less carbon atoms, such as phenyl, naphthyl, etc. As the heteroaryl groups, there may be exemplified 5- or 6-membered heteroaryl groups containing 1 to 4 nitrogen atoms, such as 2-, 3- or 4-pyridyl, pyrrolyl, indazolyl, triazolyl, tetrazolyl, etc.; and 5- or 6-membered heteroaryl groups containing 0 to 2 nitrogen atoms and an oxygen atom or a sulfur atom such as 2- or 3-furyl, 2- or 3-thienyl, 1-, 3- or 4-oxazolyl, 3-, 4- or 5-isooxazolyl, etc.

The substituent of each of the substituted aryl group and the substituted heteroaryl group includes unsubstituted alkyl groups, substituted alkyl groups, halogen atoms, nitro group, alkoxycarbonyl groups, carboxyl group, and groups represented by the formula —OR$_5$, —NR$_6$R$_7$, —CONR$_6$R$_7$, —SO2NR$_6$R$_7$ or —S(O)nR$_8$.

When R$_1$, R$_2$, R$_3$ and R$_4$ are independently a group represented by the formula —OR$_5$ wherein R$_5$ is an aromatic group, typical examples of the —OR$_5$ group are unsubstituted phenoxy group and substituted phenoxy groups. Examples of the substituted phenoxy groups are those having as the substituent, for example, a nitro group, a —NR$_6$R$_7$ group wherein R$_6$ and R$_7$ are independently, for instance, a hydrogen atom or an alkyl group, or a substituted alkyl group having as the substituent, for example, a hydroxyl group or a —NR$_6$R$_7$ group. More specific examples of the substituted phenoxy groups are o-, m- or p-nitrophenoxy, o-, m- or p-aminophenoxy, o-, m- or p-(dimethylamino)phenoxy, o-, m- or p-(amino-methyl) phenoxy, and o-, m- or p-(dimethylaminomethyl)-phenoxy.

The alkoxy group includes, for example, linear or branched alkoxy groups of 6 or less carbon atoms, such as methoxy, ethoxy, isopropoxy, tert-butoxy, etc.

As the cyclic amino group which R$_6$ and R$_7$ form when taken together with the nitrogen atom to which they are bonded, i.e., the saturated 5- to 7-membered cyclic amino group which may contain another heteroatom in the ring, there may be exemplified 5- to 7-membered cyclic groups containing 1 to 3 nitrogen atoms and 5- to 7-membered cyclic groups containing a nitrogen atom and an oxygen atom. More specific examples of the saturated 5- to 7-membered cyclic amino group are 1-pyrrolidinyl, 1-piperidino, 1-piperazinyl, 4-morpholino and 1-(4-methyl) piperazinyl.

The substituent of the substituted alkyl group includes halogen atoms, hydroxyl group, alkoxy groups, cycloalkyl groups, cyano group, carboxyl group, alkoxycarbonyl groups, aromatic groups, acyl groups and groups represented by the formula —CONR$_p$R$_q$ wherein R$_p$ and R$_q$ are independently a hydrogen atom or an alkyl group, R$_p$ and R$_q$ being able to be taken together to represent a saturated 5- to 7-membered cyclic amino group which may contain another heteroatom in the ring, the formula —NR$_6$R$_7$, or the formula:

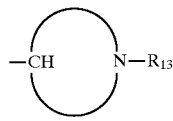

wherein R$_{13}$ is a hydrogen atom, an unsubstituted alkyl group or a substituted alkyl group and the ring is a 3- to 8-membered saturated heterocyclic ring containing a nitrogen atom. Particularly when any of R$_1$, R$_2$, R$_3$, R$_4$, R$_5$, R$_8$, R$_9$, R$_{12}$ and Z is a substituted alkyl group, the substituent includes, for example, cycloalkyl groups, halogen atoms, hydroxyl group, alkoxy groups, carboxyl group, alkoxycarbonyl groups, acyl groups, aromatic groups and groups represented by the formula —CONR$_p$R$_q$ or —NR$_6$R$_7$. When any of R$_6$, R$_7$, R$_{10}$, R$_{11}$ and R$_{13}$ is a substituted alkyl group, the substituent includes, for example, cycloalkyl groups, hydroxyl group, alkoxy groups, carboxyl group, alkoxycarbonyl groups, acyl groups, aryl groups, and groups represented by the formula —CONR$_p$R$_q$ or —NR$_6$R$_q$. As the alkyl portion of the substituted alkyl group, there may be exemplified the same groups as those exemplified above as the alkyl group.

As such substituted alkyl groups, there may be exemplified substituted alkyl groups of 1 to 5 carbon atoms having as the substituent a cycloalkyl group of 3 to 6 carbon atoms, polyhaloalkyl groups of 1 to 5 carbon atoms, hydroxyalkyl groups of 1 to 6 carbon atoms, alkoxyalkyl groups of 2 to 6 carbon atoms, cyanoalkyl groups of 2 to 6 carbon atoms, carboxyalkyl groups of 2 to 6 carbon atoms, alkoxycarbonylalkyl groups of 3 to 8 carbon atoms, alkanoylalkyl groups of 3 to 8 carbon atoms, aroylalkyl groups of 16 or less carbon atoms, substituted or unsubstituted phenyl- or naphythyl-C$_1$~C$_5$ alkyl groups, carbamoyl-C$_1$~C$_3$ alkyl groups which may have one or two C$_1$~C$_3$ alkyl groups as a substituent(s) on the nitrogen atom, amino-C$_1$~C$_5$ alkyl groups which may have one or two C$_1$~C$_3$ alkyl or C$_7$~C$_{11}$ aralkyl groups as a substituent(s) on the nitrogen atom, and saturated 5- to 7-membered cyclic amino-C$_1$~C$_3$ alkyl groups.

Typical examples of the substituted alkyl group are polyhaloalkyl groups of 1 to 3 carbon atoms, such as trifluoromethyl, trifluoroethyl, trichloromethyl, etc.; hydroxyalkyl groups of 1 to 6 carbon atoms, such as hydroxymethyl, hydroxyethyl, 1-hydroxyethyl, etc.; aminoalkyl groups of 1 to 5 carbon atoms, such as aminomethyl, aminoethyl, 1-aminoethyl, etc.; alkoxyalkyl groups of 1 to 6 carbon atoms, such as methoxyethyl, ethoxyethyl, methoxypropyl, etc.; carboxyalkyl groups of 2 to 6 carbon atoms, such as carboxyethyl, carboxypropyl, etc.; alkoxycarbonylalkyl groups of 3 to 7 carbon atoms, such as methoxycarbonylmethyl, ethoxycarbonylmethyl, methoxycarbonylethyl, etc.; phenyl- or naphythyl-C$_1$~C$_5$ alkyl groups (which may have in the phenyl or naphthyl portion a substituent such as a C$_1$~C$_3$ alkyl group, halogen atom, nitro group, amino group, hydroxyl group, C$_1$~C$_3$ alkoxy group or the like) such as benzyl, phenylethyl, phenylpropyl, phenylbutyl, 1- or 2-naphthylmethyl, etc.; carbamoyl C$_1$~C$_3$ alkyl groups which may have one or two C$_1$~C$_3$ alkyl groups as a substituent(s) on the nitrogen atom, for example, carbamoylmethyl, carbamoylethyl, dimethylcarbamoylmethyl, etc.; amino-C$_1$~C$_5$ alkyl groups which may have one or two C$_1$~C$_3$ alkyl or C$_7$~C$_{11}$ aralkyl groups as a substituent(s) on the nitrogen atom, for example, aminoethyl, aminopropyl, dimethylaminoethyl, dimethylaminopropyl, diethylaminoethyl, N-methyl-N-benzylaminoethyl, etc.; and saturated 5- to 7-membered cyclic amino-C$_1$~C$_3$ alkyl groups such as 1-pyrrolidinylethyl, piperidinoethyl, etc. In the case of R$_6$ and R$_7$, typical examples of the substituted alkyl group are phenyl-C$_1$~C$_5$ alkyl groups such as phenylethyl, etc.

As the substituent on the lower alkylene group for Q and the substituent on the vinyl or ethynyl group for Ra, there may be exemplified unsubstituted alkyl groups, substituted alkyl groups, cycloalkyl groups, cycloalkenyl groups, saturated heterocyclic groups, carboxyl group, alkoxycarbonyl groups, aromatic groups, and groups represented by the formula —CON(R$_6$)R$_7$.

The lower alkylene group includes, for example, alkylene groups of 6 or less carbon atoms, such as methylene, ethylene, trimethylene, tetramethylene, pentamethylene, hexamethylene, etc.

The acyl group includes, for example, formyl group; alkanoyl groups of 2 to 6 carbon atoms, such as acetyl, propanoyl, etc.; cycloalkanecarbonyl groups of 3 to 6 carbon atoms, such as cyclopropanecarbonyl, cyclobutanecarbonyl, cyclopentanecarbonyl, cyclohexanecarbonyl, etc.; cycloalkenecarbonyl groups of 3 to 6 carbon atoms, such as cyclopentenecarbonyl, cyclohexenecarbonyl, etc.; aroyl groups of 6 to 10 carbon atoms, such as benzoyl, toluoyl, naphthoyl, etc.; saturated heterocyclic ring-carbonyl groups having a 5- or 6-membered saturated heterocyclic ring containing one or two heteroatoms selected from the group consisting of nitrogen atom, oxygen atom and sulfur atom, for example, 2-piperidinecarbonyl, 3-morpholinecarbonyl, etc.; and heteroaromatic acyl groups having a 5- or 6-membered heteroaromatic ring containing one or two heteroatoms selected from the group consisting of nitrogen atom, oxygen atom and sulfur atom, for example, furoyl, thenoyl, nicotinoyl, isonicotinoyl, etc.

As the cyclic amino group which Rp and Rq form when taken together, i.e., the saturated 5- to 7-membered cyclic amino group which may contain another hetero atom in the ring, there may be exemplified the same groups as those exemplified above as the cyclic amino group formed by R$_6$ and R$_7$.

The group represented by the formula —S(O)nR$_8$ includes, for example, alkylsulfonyl groups of 8 or less carbon atoms, such as methylsulfonyl, ethylsulfonyl, propylsulfonyl, isopropylsulfonyl, etc., and alkylsulfinyl groups and alkylthio groups, which correspond the alkylsulfonyl groups.

As the group represented by the formula:

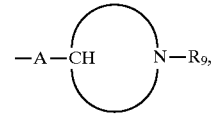

there may be exemplified groups represented by the following formulas:

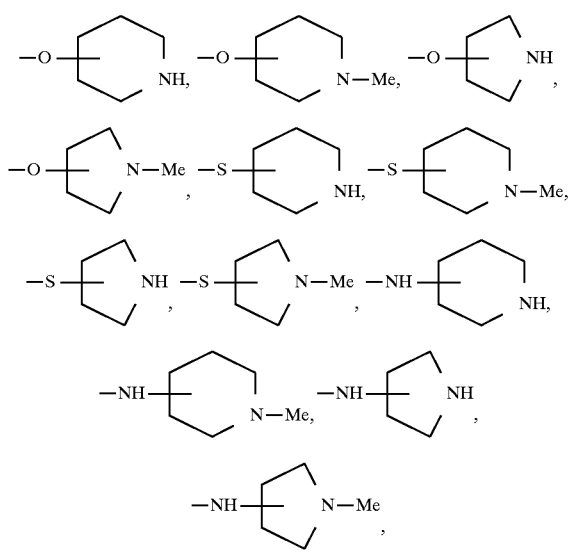

Preferable examples of said group are (piperidin-3-yl)oxy, (piperidin-4-yl)oxy, (1-methylpiperidin-3-yl)oxy, (1-methylpiperidin-4-yl)oxy, (pyrrolidin-3-yl)oxy, (1-methylpyrrolidin-3-yl)oxy, (piperidin-3-yl)thio, (piperidin-4-yl)thio, (1-methylpiperidin-3-yl)thio, (1-methylpiperidin-4-yl)thio, (pyrrolidin-3-yl)thio, (1-methylpyrrolidin-2-yl)thio, (piperidin-3-yl)amino, (piperidin-4-yl)amino, (1-methylpiperidin-3-yl)amino, (1-methylpiperidin-4-yl)amino, (pyrrolidin-3-yl)amino and (1-methylpyrrolidin-3-yl)amino.

The alkenyl group includes, for example, alkenyl groups of 6 or less carbon atoms, such as vinyl, allyl, propenyl, 2-propenyl, butenyl, pentenyl, hexenyl, etc.

The alkynyl group includes, for example, alkynyl groups of 6 or less carbon atoms, such as ethynyl, propargyl, butynyl, pentynyl, etc.

In addition, the present invention relates to a process for producing the compound of the above formula (1). The process comprises reacting a carboxylic acid reactive derivative of the formula (2):

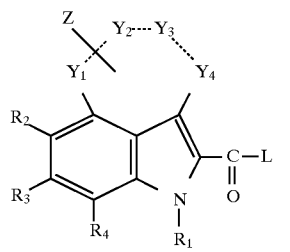

(2)

wherein $R_1$, $R_2$, $R_3$, $R_4$, $Y_1$, $Y_2$, $Y_3$, $Y_4$ and Z are as defined above, and L is a leaving group easily replaceable by a nucleophilic reagent, with guanidine to form the guanidinocarbonyl group (—C(=O)N=C(NH$_2$)$_2$ group) shown in the formula (1) and, if necessary, converting the reaction product to a pharmaceutically acceptable salt.

In the above reaction, when the acid derivative of the formula (2) has a reactive group such as hydroxyl group or amino group, the reactive group is previously protected with a suitable protective group, and the protective group is removed after carrying out the reaction, whereby a desired acylguanidine derivative (1) may be produced.

As the carboxylic acid reactive derivative of the formula (2), there may be exemplified acid halides, acid anhydrides (including mixed acid anhydrides) and ester derivatives. Specific examples of the carboxylic acid reactive derivative are acid halides such as acid chlorides and acid bromides; mixed acid anhydrides of an alkyloxychloride type compound (e.g. ethyloxycarbonyl chloride or isobutyloxycarbonyl chloride) and an α-polyalkyl-substituted carboxylic acid chloride type compound (e.g. diethylacetyl chloride or trimethylacetyl chloride); and ester derivatives such as activated esters (e.g. p-nitrophenyl esters, N-hydroxysuccinimide esters and pentafluorophenyl esters) and common esters (e.g. methyl esters and ethyl esters). Such a carboxylic acid reactive derivative can easily be obtained from a corresponding carboxylic acid according to a conventional method.

When guanidine is reacted with the acid halide or the acid anhydride (including the mixed acid anhydride), the reaction may be carried out in a solvent in the presence of a base or excess guanidine with cooling or at room temperature. As the base, there may be exemplified inorganic bases such as sodium hydroxide, potassium hydroxide, sodium carbonate, potassium carbonate, sodium hydrogencarbonate, etc.; and organic bases such as triethylamine, pyridine, etc. As the solvent, there may be exemplified aromatic hydrocarbon solvents such as benzene, toluene, xylene, etc.; ether solvents such as tetrahydrofuran, 1,4-dioxane, etc.; halogenated hydrocarbon solvents such as dichloromethane, chloroform, 1,2-dichloroethane, etc.; amide solvents such as dimethylformamide, dimethylacetamide, etc.; basic solvents such as pyridine, etc.; and mixed solvents thereof.

When guanidine is reacted with the ester derivative, the reaction is carried out in a solvent in the presence of an equimolar or excess amount of guanidine with heating or cooling. When the ester derivative is the activated ester, the reaction is preferably carried out, for example, in an ether solvent (e.g. tetrahydrofuran, 1,2-dimethoxyethane or dioxane), an ester solvent (e.g. ethyl acetate), dimethylformamide, or a mixed solvent thereof. When the ester derivative is other than the activated esters, the reaction is preferably carried out, for example, in an alcohol solvent (e.g. methanol, ethanol or isopropanol), an ether solvent (e.g. tetrahydrofuran, 1,2-dimethoxyethane or dioxane), dimethylformamide, or a mixed solvent thereof. After the solvent is distilled off, the residue may be heated for a short time at about 130° C. if necessary.

The compound (1) of the present invention may be obtained by reacting a carboxylic acid of the general formula (3):

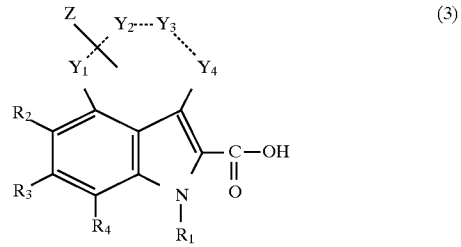

(3)

wherein $R_1$, $R_2$, $R_3$, $R_4$, $Y_1$, $Y_2$, $Y_3$, $Y_4$ and Z are as defined above, with guanidine preferably in the presence of a condensing agent in an inert solvent at room temperature or with heating.

In this reaction, when the compound of the formula (3) has a reactive group such as carboxyl group, hydroxyl group or amino group, the reactive group is previously protected with a suitable protective group, and the protective group is removed after carrying out the reaction, whereby a desired acylguanidine derivative (1) may be produced.

The reaction is preferably carried out in the presence of a condensing agent (e.g. dicyclohexylcarboduimide (DCC), diisopropylcarbodiimide (DIPC), 1-ethyl-3-(3-dimethylaminopropyl)carbodiimide (WSC), benzotriazol-1-yl-tris(dimethylamino)phosphoniumhexafluorophosphate (BOP), diphenylphosphonylazide (DPPA), N,N-carbonyldiimidazole (Angew. Chem. Int. Ed. Engl., Vol. 1, 351(1962)] and optionally an additive [e.g. N-hydroxysuccinimide (HONSu), 1-hydroxybenzotriazole (HObt) or 3-hydroxy-4-oxo-3,4-dihydro-1,2,3-benzotriazine (HOObt)] in an aromatic hydrocarbon solvent (e.g benzene, toluene or xylene), an ether solvent (e.g. tetrahydrofuran or 1,4-dioxane), a halogenated hydrocarbon solvent (dichloromethane, chloroform or 1,2-dichloroethane), an amide solvent (dimethylformamide or dimethylacetamide), a basic solvent (e.g. pyridine) or a mixed solvent thereof.

In the above-mentioned production, as the protective group for the reactive group such as hydroxyl, amino or carboxyl, protective groups conventionally used in the field of organic synthetic chemistry may be used. The introduction and removal of such a protective group may be carried out by a conventional method (for example, Protective Groups in Organic Synthesis, JOHN WILLEY & SONS, 1991).

The protective group for the hydroxyl group includes, for example, methoxymethyl group and tetrahydropyranyl group. The protective group for the amino group includes, for example, tert-butoxycarbonyl group. The protective group for the hydroxyl group may be removed by reaction in a solvent such as aqueous methanol, aqueous ethanol or aqueous tetrahydrofuran in the presence of an acid such as hydrochloric acid, sulfuric acid or acetic acid. The protective group for the amino group may be removed by reaction in a solvent such as aqueous tetrahydrofuran, methylene chloride, chloroform or aqueous methanol in the presence of an acid such as hydrochloric acid or trifluoroacetic acid.

The carboxyl group is protected, for example, in the form of a tert-butyl ester, orthoester or acid amide. The protective group used for this protection is removed as follows. In the case of the tert-butyl ester, the removal is carried out, for example, by reaction in an aqueous solvent in the presence of hydrochloric acid. In the case of the orthoester, the removal is carried out by treatment with an acid and then an alkali such as sodium hydroxide in a solvent such as aqueous methanol, aqueous tetrahydrofuran or aqueous 1,2-dimethoxyethane. In the case of the acid amide, the removal is carried out by reaction in a solvent such as water, aqueous methanol or aqueous tetrahydrofuran in the presence of an acid such as hydrochloric acid or sulfuric acid.

The carboxylic acid derivative of the general formula (2) and the carboxylic acid of the general formula (3), i.e., the starting compounds in the above-mentioned production processes, respectively, are known in the following literature or may be produced by the same processes as described in the literature:
(1) Japanese Patent Unexamined Publication No. 7-188166
(2) Chem. Pharm. Bull. (1977), 25, 3023–3033
(3) J. Med. Chem. (1994), 37, 1153–1164
(4) J. Am. Chem. Soc. (1955), 77, 3334–3336
(5) Japanese Patent Unexamined Publication No. 63-501361, etc.

The carboxylic acid of the general formula (3) can easily be derived from an ester of the general formula (1e) shown below, by a conventional hydrolysis reaction. The carboxylic acid reactive derivative of the general formula (2) may be synthesized from the carboxylic acid of the general formula (3) according to a conventional process.

A process for synthesizing the ester of the general formula (1e) is described below.
Synthesis Process-1
The compound of the general formula (1e) may be synthesized according to the following reaction formula:

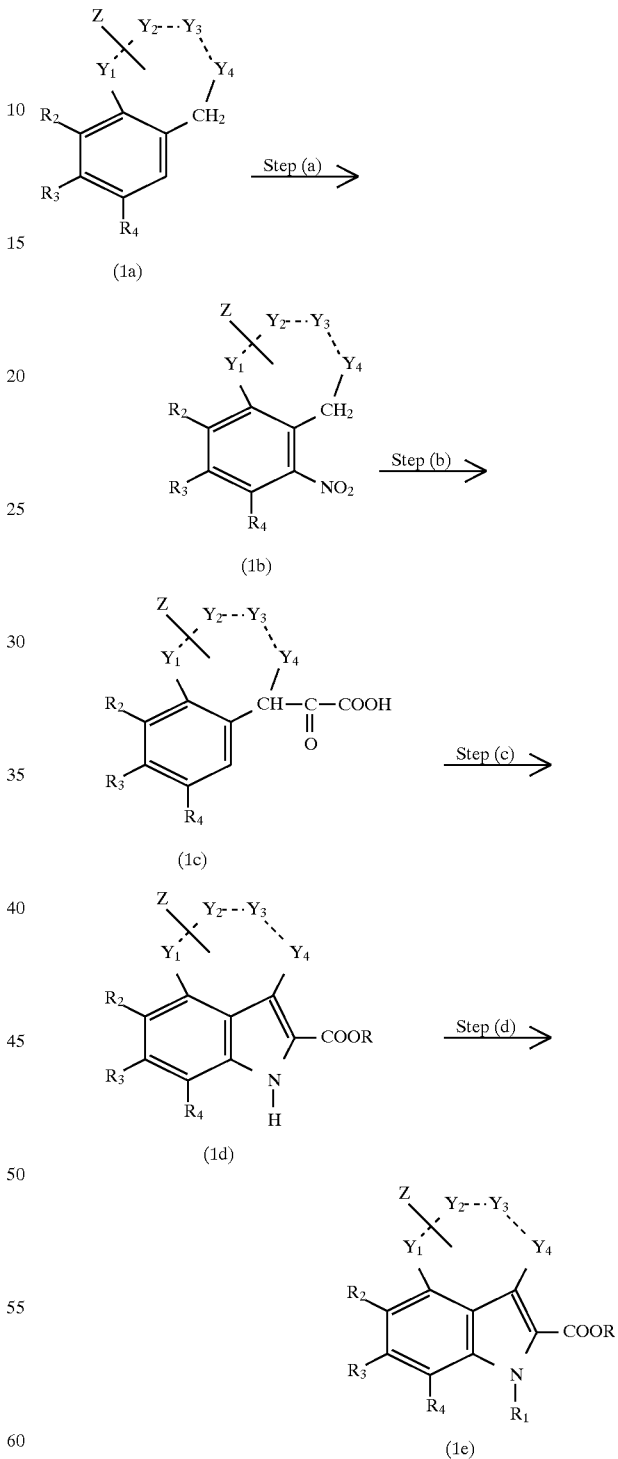

wherein $R_1$, $R_2$, $R_3$, $R_4$, $Y_1$, $Y_2$, $Y_3$, $Y_4$ and Z are as defined above, and R is a lower alkyl group.

The nitration in the step (a) may be carried out with a nitrating agent such as concentrated nitric acid, fuming nitric acid or sodium nitrate in a mineral acid or an organic carboxylic acid. It may be carried out also by treatment with nitronium tetrafluoroborate in a halogenated hydrocarbon solvent such as chloroform or methylene chloride.

The acylation in the step (b) is carried out by reacting the nitration product with an oxalic acid diester such as diethyl oxalate in an inert protic or aprotic solvent in the presence of a strong base. The solvent used in this step includes ethers (e.g. diethyl ether and tetrahydrofuran), N,N-dimethylformamide, dimethyl sulfoxide, alcohols (e.g. methanol and ethanol), benzene and mixtures of these solvents. The base used in this step includes lithium diisopropylamide, n-butyllithium, sodium hydride, and metal alkoxides (e.g. sodium methoxide, potassium ethoxide and potassium tert-butoxide).

The reduction and ring-closing reaction in the step (c) may be carried out with a reducing agent such as an aqueous titanium trichloride solution, tin chloride, zinc, iron powder, formic acid-palladium carbon, or the like in a protic solvent (e.g. methanol, ethanol or acetic acid) or an aprotic solvent (acetone, tetrahydrofuran, toluene or N,N-dimethylformamide).

The step (d) is carried out by reacting the thus obtained compound with a compound of the formula $R_1X$ wherein $R_1$ is as defined above and X is a leaving group such as fluorine, chlorine, bromine, iodine, methanesulfonyloxy, p-toluenesulfonyloxy, trifluoro-methanesulfonyloxy or the like, in the presence of a base in an inert solvent such as N,N-dimethylformamide or tetrahydrofuran. The base used in this step includes inorganic bases (e.g. potassium carbonate and sodium carbonate), organic bases (e.g. triethylamine and pyridine), alkali metal hydrides (e.g. sodium hydride and potassium hydride), etc.

Synthesis Process-2

A compound of the general formula (2f) may be synthesized according to the following reaction formula:

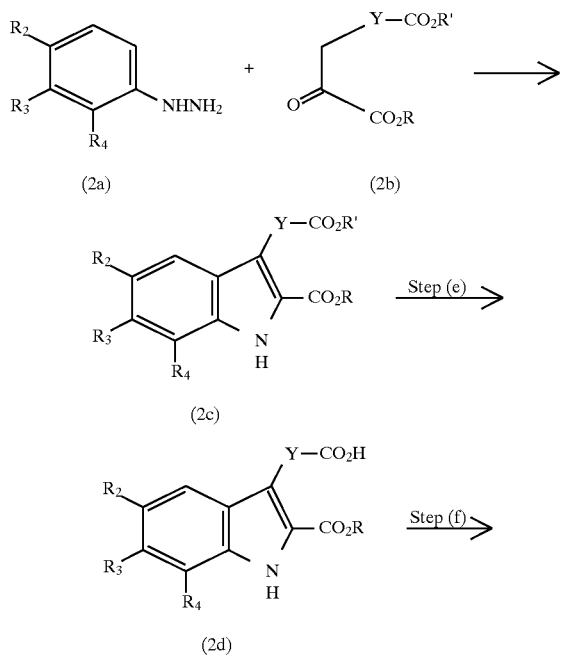

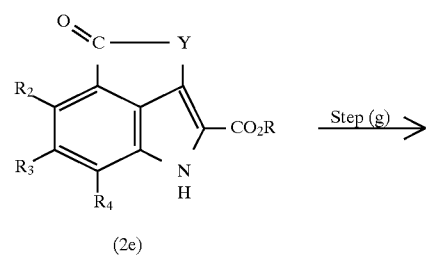

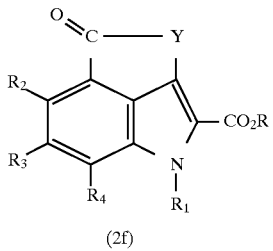

wherein $R_1$, $R_2$, $R_3$, $R_4$ and R are as defined above, R' is a lower alkyl group, and Y is an unsubstituted alkylene chain of 2 or 3 carbon atoms or a substituted alkylene chain of 2 or 3 carbon atoms having the above-mentioned substituent Z.

A compound of the formula (2c) may be prepared by Fischer's indole condensation by reacting a phenylhydrazine (2a) with a ketone (2b) in an inert solvent (e.g. toluene, benzene or tetrahydrofuran) in the presence of an acid (e.g. acetic acid or p-toluenesulfonic acid) according to the same method as that well known in literature (e.g. Japanese Patent Unexamined Publication Nos. 48-22495 and 6-287192).

The hydrolysis in the step (e) may be carried out under acidic conditions (for example, acetic acid-sulfuric acid).

The ring-closing reaction in the step (f) may be carried out by employing the generally known Friedel-Crafts reaction. A method for carrying out this step is, for example, as follow: a carboxylic acid of the formula (2d) is converted to an acid halide with thionyl chloride, phosphorus pentachloride or the like, after which the acid halide may be subjected to ring-closing reaction by using a Lewis acid such as aluminum chloride, antimony pentachloride, iron trichloride, tin tetrachloride, titanium tetrachloride, zinc chloride, boron trifluoride or the like. As a solvent used in the step (f), there may be used nitrobenzene, 1,2-dichloroethane, chloroform, acetone, tetrahydrofuran, ethyl acetate, etc. As an alternate method, it is possible to carry out the ring-closing reaction by reacting the carboxylic acid in a polyphosphoric acid (PPA).

The step (g) may be carried out in the same manner as in the step (d) described above. Further, the compound (2f) may be converted to any of, for example, the compounds (2g), (2h) and (2i) shown in the following scheme:

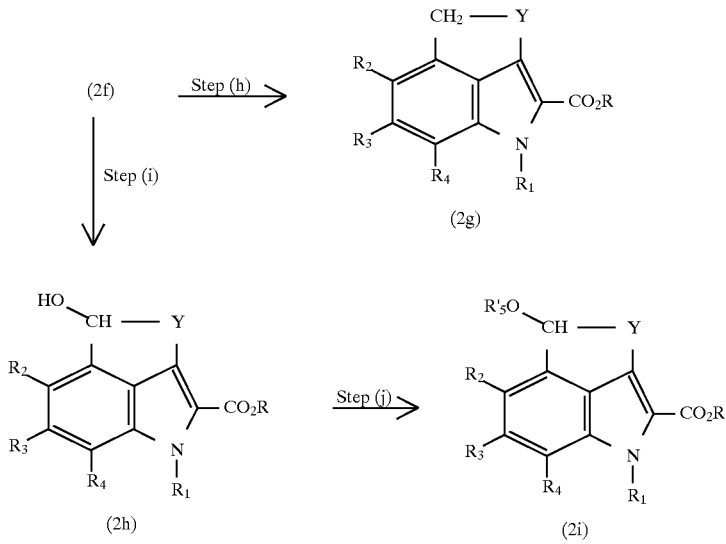

wherein $R_1$, $R_2$, $R_3$, $R_4$, Y and R are as defined above. $R'_5$ has the same meaning as defined above for $R_5$ but is not a hydrogen atom.

The reduction in the step (h) may be carried out, for example, with triethylsilane in trifluoroacetic acid.

The reduction in the step (i) may be carried out, for example, with sodium borohydride.

The step (j) may be carried out in the same manner as for the above-mentioned step (d).

Synthesis Process-3

A compound of the general formula (3d) may be synthesized according to the following reaction formula:

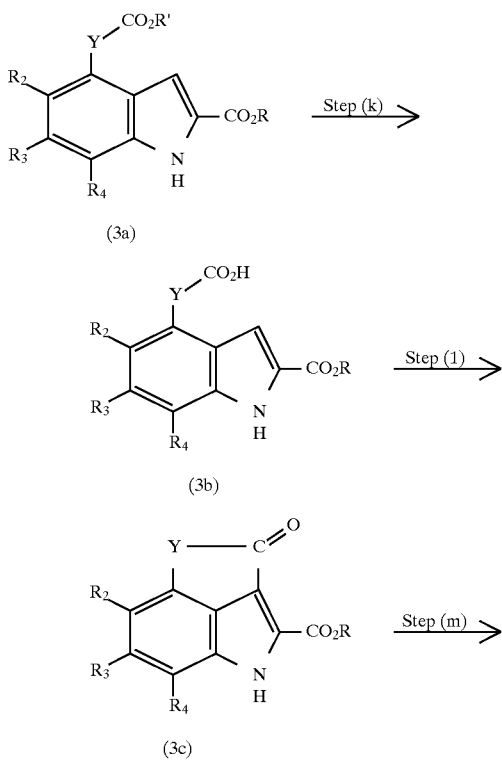

-continued

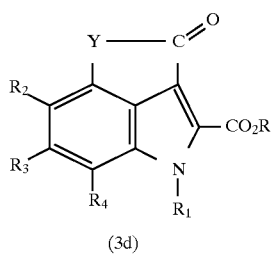

wherein $R_1$, $R_2$, $R_3$, $R_4$, Y, R and R' are as defined above.

Usually, an indole-2-carboxylic acid derivative of the formula (3a) may be prepared by any of Fischer's indole condensation, Reisert's reaction, Hemetsberger's process, etc. which are well known as processes for synthesizing indole-2-carboxylic acid.

The hydrolysis in the step (k) may be carried out in the same manner as for the above-mentioned step (e).

The ring-closing reaction in the step (l) may be carried out in the same manner as for the above-mentioned step (f).

The step (m) may be carried out in the same manner as for the above-mentioned step (d).

Further, the compound (3d) may be converted to any of, for example, the compounds (3e), (3f) and (3g) shown in the following scheme:

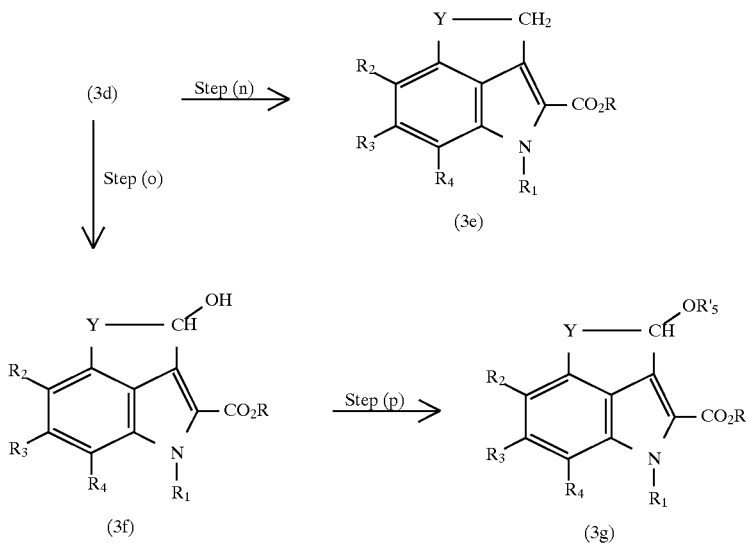

wherein $R_1$, $R_2$, $R_3$, $R_4$, Y, R and $R'_5$ are as defined above.

The steps (n), (o) and (p) may be carried out in the same manner as for the above-mentioned steps (h), (i) and (j), respectively.

In each of the above synthesis processes 1 to 3, when the intermediate compound used in any of the steps has a reactive group such as carboxyl, hydroxyl or amino, the reactive group is previously protected with a suitable protective group, and the protective group is removed if necessary after carrying out the reaction, whereby a desired compound of the general formula (2) or (3) may be produced.

As the compound of the general formula (1) produced in the manner described above, the compounds listed in Table 1 may be exemplified.

TABLE 1

| $R_1$ | $R_2$ | $R_3$ | $R_4$ | -v- | -w- | -x- |
|---|---|---|---|---|---|---|
| H | $CH_3$ | H | H | $-CH_2-$ | $-CH_2-$ | $-CH_2-$ |
| H | H | $CH_3$ | H | $-CH_2-$ | $-CH_2-$ | $-CH_2-$ |
| H | H | H | $CH_3$ | $-CH_2-$ | $-CH_2-$ | $-CH_2-$ |
| H | $OCH_3$ | H | H | $-CH_2-$ | $-CH_2-$ | $-CH_2-$ |
| H | H | $OCH_3$ | H | $-CH_2-$ | $-CH_2-$ | $-CH_2-$ |
| H | H | H | $OCH_3$ | $-CH_2-$ | $-CH_2-$ | $-CH_2-$ |
| H | Cl | H | H | $-CH_2-$ | $-CH_2-$ | $-CH_2-$ |
| H | H | Cl | H | $-CH_2-$ | $-CH_2-$ | $-CH_2-$ |
| H | H | H | Cl | $-CH_2-$ | $-CH_2-$ | $-CH_2-$ |
| H | F | H | H | $-CH_2-$ | $-CH_2-$ | $-CH_2-$ |
| H | H | F | H | $-CH_2-$ | $-CH_2-$ | $-CH_2-$ |
| H | H | H | F | $-CH_2-$ | $-CH_2-$ | $-CH_2-$ |
| H | $CF_3$ | H | H | $-CH_2-$ | $-CH_2-$ | $-CH_2-$ |
| H | H | $CF_3$ | H | $-CH_2-$ | $-CH_2-$ | $-CH_2-$ |
| H | H | H | $CF_3$ | $-CH_2-$ | $-CH_2-$ | $-CH_2-$ |
| $CH_3$ | $CH_3$ | H | H | $-CH_2-$ | $-CH_2-$ | $-CH_2-$ |
| $CH_3$ | H | $CH_3$ | H | $-CH_2-$ | $-CH_2-$ | $-CH_2-$ |
| $CH_3$ | H | H | $CH_3$ | $-CH_2-$ | $-CH_2-$ | $-CH_2-$ |
| $CH_3$ | $OCH_3$ | H | H | $-CH_2-$ | $-CH_2-$ | $-CH_2-$ |
| $CH_3$ | H | $OCH_3$ | H | $-CH_2-$ | $-CH_2-$ | $-CH_2-$ |
| $CH_3$ | H | H | $OCH_3$ | $-CH_2-$ | $-CH_2-$ | $-CH_2-$ |
| $CH_3$ | Cl | H | H | $-CH_2-$ | $-CH_2-$ | $-CH_2-$ |
| $CH_3$ | H | Cl | H | $-CH_2-$ | $-CH_2-$ | $-CH_2-$ |
| $CH_3$ | H | H | Cl | $-CH_2-$ | $-CH_2-$ | $-CH_2-$ |
| $CH_3$ | F | H | H | $-CH_2-$ | $-CH_2-$ | $-CH_2-$ |

TABLE 1-continued

| R1 | R2 | R3 | R4 | V | W | X |
|---|---|---|---|---|---|---|
| CH₃ | H | F | H | —CH₂— | —CH₂— | —CH₂— |
| CH₃ | H | H | F | —CH₂— | —CH₂— | —CH₂— |
| CH₃ | CF₃ | H | H | —CH₂— | —CH₂— | —CH₂— |
| CH₃ | H | CF₃ | H | —CH₂— | —CH₂— | —CH₂— |
| CH₃ | H | H | CF₃ | —CH₂— | —CH₂— | —CH₂— |
| CH(CH₃)₂ | CH₃ | H | H | —CH₂— | —CH₂— | —CH₂— |
| CH(CH₃)₂ | H | CH₃ | H | —CH₂— | —CH₂— | —CH₂— |
| CH(CH₃)₂ | H | H | CH₃ | —CH₂— | —CH₂— | —CH₂— |
| CH(CH₃)₂ | OCH₃ | H | H | —CH₂— | —CH₂— | —CH₂— |
| CH(CH₃)₂ | H | OCH₃ | H | —CH₂— | —CH₂— | —CH₂— |
| CH(CH₃)₂ | H | H | OCH₃ | —CH₂— | —CH₂— | —CH₂— |
| CH(CH₃)₂ | Cl | H | H | —CH₂— | —CH₂— | —CH₂— |
| CH(CH₃)₂ | H | Cl | H | —CH₂— | —CH₂— | —CH₂— |
| CH(CH₃)₂ | H | H | Cl | —CH₂— | —CH₂— | —CH₂— |
| CH(CH₃)₂ | F | H | H | —CH₂— | —CH₂— | —CH₂— |
| CH(CH₃)₂ | H | F | H | —CH₂— | —CH₂— | —CH₂— |
| CH(CH₃)₂ | H | H | F | —CH₂— | —CH₂— | —CH₂— |
| CH(CH₃)₂ | CF₃ | H | H | —CH₂— | —CH₂— | —CH₂— |
| CH(CH₃)₂ | H | CF₃ | H | —CH₂— | —CH₂— | —CH₂— |
| CH(CH₃)₂ | H | H | CF₃ | —CH₂— | —CH₂— | —CH₂— |
| CH₂Ph | CH₃ | H | H | —CH₂— | —CH₂— | —CH₂— |
| CH₂Ph | H | CH₃ | H | —CH₂— | —CH₂— | —CH₂— |
| CH₂Ph | H | H | CH₃ | —CH₂— | —CH₂— | —CH₂— |
| CH₂Ph | OCH₃ | H | H | —CH₂— | —CH₂— | —CH₂— |
| CH₂Ph | H | OCH₃ | H | —CH₂— | —CH₂— | —CH₂— |
| CH₂Ph | H | H | OCH₃ | —CH₂— | —CH₂— | —CH₂— |
| CH₂Ph | Cl | H | H | —CH₂— | —CH₂— | —CH₂— |
| CH₂Ph | H | Cl | H | —CH₂— | —CH₂— | —CH₂— |
| CH₂Ph | H | H | Cl | —CH₂— | —CH₂— | —CH₂— |
| CH₂Ph | F | H | H | —CH₂— | —CH₂— | —CH₂— |
| CH₂Ph | H | F | H | —CH₂— | —CH₂— | —CH₂— |
| CH₂Ph | H | H | F | —CH₂— | —CH₂— | —CH₂— |
| CH₂Ph | CF₃ | H | H | —CH₂— | —CH₂— | —CH₂— |
| CH₂Ph | H | CF₃ | H | —CH₂— | —CH₂— | —CH₂— |
| CH₂Ph | H | H | CF₃ | —CH₂— | —CH₂— | —CH₂— |
| CH₂CH₂OCH₃ | CH₃ | H | H | —CH₂— | —CH₂— | —CH₂— |
| CH₂CH₂OCH₃ | H | CH₃ | H | —CH₂— | —CH₂— | —CH₂— |
| CH₂CH₂OCH₃ | H | H | CH₃ | —CH₂— | —CH₂— | —CH₂— |
| CH₂CH₂OCH₃ | OCH₃ | H | H | —CH₂— | —CH₂— | —CH₂— |
| CH₂CH₂OCH₃ | H | OCH₃ | H | —CH₂— | —CH₂— | —CH₂— |
| CH₂CH₂OCH₃ | H | H | OCH₃ | —CH₂— | —CH₂— | —CH₂— |
| CH₂CH₂OCH₃ | Cl | H | H | —CH₂— | —CH₂— | —CH₂— |
| CH₂CH₂OCH₃ | H | Cl | H | —CH₂— | —CH₂— | —CH₂— |
| CH₂CH₂OCH₃ | H | H | Cl | —CH₂— | —CH₂— | —CH₂— |
| CH₂CH₂OCH₃ | F | H | H | —CH₂— | —CH₂— | —CH₂— |
| CH₂CH₂OCH₃ | H | F | H | —CH₂— | —CH₂— | —CH₂— |
| CH₂CH₂OCH₃ | H | H | F | —CH₂— | —CH₂— | —CH₂— |
| CH₂CH₂OCH₃ | CF₃ | H | H | —CH₂— | —CH₂— | —CH₂— |
| CH₂CH₂OCH₃ | H | CF₃ | H | —CH₂— | —CH₂— | —CH₂— |
| CH₂CH₂OCH₃ | H | H | CF₃ | —CH₂— | —CH₂— | —CH₂— |
| H | H | H | H | —CH(CH₃)— | —CH₂— | —CH₂— |
| CH₃ | H | H | H | —CH(CH₃)— | —CH₂— | —CH₂— |
| CH(CH₃)₂ | H | H | H | —CH(CH₃)— | —CH₂— | —CH₂— |
| CH₂Ph | H | H | H | —CH(CH₃)— | —CH₂— | —CH₂— |
| CH₂CH₂OCH₃ | H | H | H | —CH(CH₃)— | —CH₂— | —CH₂— |
| H | H | H | H | —CO— | —CH₂— | —CH₂— |
| CH₃ | H | H | H | —CO— | —CH₂— | —CH₂— |
| CH(CH₃)₂ | H | H | H | —CO— | —CH₂— | —CH₂— |
| CH₂Ph | H | H | H | —CO— | —CH₂— | —CH₂— |
| CH₂CH₂OCH₃ | H | H | H | —CO— | —CH₂— | —CH₂— |
| H | F | H | H | —C(=CH₂)— | —CH₂— | —CH₂— |
| CH₃ | H | F | H | —C(=CH₂)— | —CH₂— | —CH₂— |
| CH(CH₃)₂ | H | H | F | —C(=CH₂)— | —CH₂— | —CH₂— |
| CH₂Ph | CF₃ | H | H | —C(=CH₂)— | —CH₂— | —CH₂— |
| CH₂CH₂OCH₃ | H | CF₃ | H | —C(=CH₂)— | —CH₂— | —CH₂— |

TABLE 1-continued

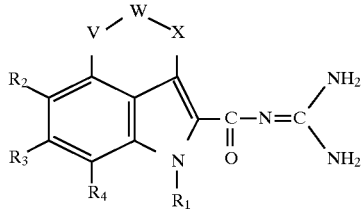

| $R_1$ | $R_2$ | $R_3$ | $R_4$ | -v-w- | -x- |
|---|---|---|---|---|---|
| H | H | H | H | —CH=CH— | —CH$_2$— |
| CH$_3$ | H | H | H | —CH=CH— | —CH$_2$— |
| CH(CH$_3$)$_2$ | H | H | H | —CH=CH— | —CH$_2$— |
| CH$_2$Ph | H | H | H | —CH=CH— | —CH$_2$— |
| CH$_2$CH$_2$OCH$_3$ | H | H | H | —CH=CH— | —CH$_2$— |

| $R_1$ | $R_2$ | $R_3$ | $R_4$ | -v- | -w-x- |
|---|---|---|---|---|---|
| H | H | H | H | —CH$_2$— | —CH=CH— |
| CH$_3$ | H | H | H | —CH$_2$— | —CH=CH— |
| CH(CH$_3$)$_2$ | H | H | H | —CH$_2$— | —CH=CH— |
| CH$_2$Ph | H | H | H | —CH$_2$— | —CH=CH— |
| CH$_2$CH$_2$OCH$_3$ | H | H | H | —CH$_2$— | —CH=CH— |

| $R_1$ | $R_2$ | $R_3$ | $R_4$ | -v- | -w- | -x- |
|---|---|---|---|---|---|---|
| H | H | H | H | —CH$_2$— | —CH$_2$— | —CO— |
| CH$_3$ | H | H | H | —CH$_2$— | —CH$_2$— | —CO— |
| CH(CH$_3$)$_2$ | H | H | H | —CH$_2$— | —CH$_2$— | —CO— |
| CH$_2$Ph | H | H | H | —CH$_2$— | —CH$_2$— | —CO— |
| CH$_2$CH$_2$OCH$_3$ | H | H | H | —CH$_2$— | —CH$_2$— | —CO— |
| H | H | H | H | —CH$_2$— | —CH$_2$— | —C(=CH$_2$)— |
| CH$_3$ | H | H | H | —CH$_2$— | —CH$_2$— | —C(=CH$_2$)— |
| CH(CH$_3$)$_2$ | H | H | H | —CH$_2$— | —CH$_2$— | —C(=CH$_2$)— |
| CH$_2$Ph | H | H | H | —CH$_2$— | —CH$_2$— | —C(=CH$_2$)— |
| CH$_2$CH$_2$OCH$_3$ | H | H | H | —CH$_2$— | —CH$_2$— | —C(=CH$_2$)— |
| H | F | H | H | —CH$_2$— | —CH$_2$— | —CH(CH$_3$)— |
| CH$_3$ | H | F | H | —CH$_2$— | —CH$_2$— | —CH(CH$_3$)— |
| CH(CH$_3$)$_2$ | H | H | F | —CH$_2$— | —CH$_2$— | —CH(CH$_3$)— |
| CH$_2$Ph | CF$_3$ | H | H | —CH$_2$— | —CH$_2$— | —CH(CH$_3$)— |
| CH$_2$CH$_2$OCH$_3$ | H | CF$_3$ | H | —CH$_2$— | —CH$_2$— | —CH(CH$_3$)— |

The compounds listed in Table 2 may be produced in the same manner as above.

TABLE 2

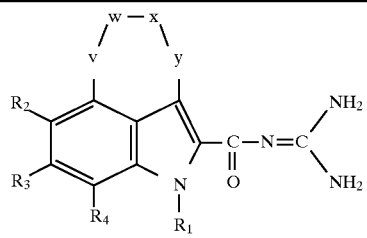

| $R_1$ | $R_2$ | $R_3$ | $R_4$ | -v- | -w- | -x- | -y- |
|---|---|---|---|---|---|---|---|
| H | CH$_3$ | H | H | —CH$_2$— | —CH$_2$— | —CH$_2$— | —CH$_2$— |
| H | H | CH$_3$ | H | —CH$_2$— | —CH$_2$— | —CH$_2$— | —CH$_2$— |
| H | H | H | CH$_3$ | —CH$_2$— | —CH$_2$— | —CH$_2$— | —CH$_2$— |
| H | OCH$_3$ | H | H | —CH$_2$— | —CH$_2$— | —CH$_2$— | —CH$_2$— |
| H | H | OCH$_3$ | H | —CH$_2$— | —CH$_2$— | —CH$_2$— | —CH$_2$— |
| H | H | H | OCH$_3$ | —CH$_2$— | —CH$_2$— | —CH$_2$— | —CH$_2$— |
| H | Cl | H | H | —CH$_2$— | —CH$_2$— | —CH$_2$— | —CH$_2$— |
| H | H | Cl | H | —CH$_2$— | —CH$_2$— | —CH$_2$— | —CH$_2$— |
| H | H | H | Cl | —CH$_2$— | —CH$_2$— | —CH$_2$— | —CH$_2$— |
| H | F | H | H | —CH$_2$— | —CH$_2$— | —CH$_2$— | —CH$_2$— |

TABLE 2-continued

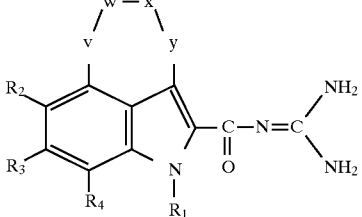

| R1 | R2 | R3 | R4 | v | w | x | y |
|---|---|---|---|---|---|---|---|
| H | H | F | H | —CH₂— | —CH₂— | —CH₂— | —CH₂— |
| H | H | H | F | —CH₂— | —CH₂— | —CH₂— | —CH₂— |
| H | CF₃ | H | H | —CH₂— | —CH₂— | —CH₂— | —CH₂— |
| H | H | CF₃ | H | —CH₂— | —CH₂— | —CH₂— | —CH₂— |
| H | H | H | CF₃ | —CH₂— | —CH₂— | —CH₂— | —CH₂— |
| CH₃ | CH₃ | H | H | —CH₂— | —CH₂— | —CH₂— | —CH₂— |
| CH₃ | H | CH₃ | H | —CH₂— | —CH₂— | —CH₂— | —CH₂— |
| CH₃ | H | H | CH₃ | —CH₂— | —CH₂— | —CH₂— | —CH₂— |
| CH₃ | OCH₃ | H | H | —CH₂— | —CH₂— | —CH₂— | —CH₂— |
| CH₃ | H | OCH₃ | H | —CH₂— | —CH₂— | —CH₂— | —CH₂— |
| CH₃ | H | H | OCH₃ | —CH₂— | —CH₂— | —CH₂— | —CH₂— |
| CH₃ | Cl | H | H | —CH₂— | —CH₂— | —CH₂— | —CH₂— |
| CH₃ | H | Cl | H | —CH₂— | —CH₂— | —CH₂— | —CH₂— |
| CH₃ | H | H | Cl | —CH₂— | —CH₂— | —CH₂— | —CH₂— |
| CH₃ | F | H | H | —CH₂— | —CH₂— | —CH₂— | —CH₂— |
| CH₃ | H | F | H | —CH₂— | —CH₂— | —CH₂— | —CH₂— |
| CH₃ | H | H | F | —CH₂— | —CH₂— | —CH₂— | —CH₂— |
| CH₃ | CF₃ | H | H | —CH₂— | —CH₂— | —CH₂— | —CH₂— |
| CH₃ | H | CF₃ | H | —CH₂— | —CH₂— | —CH₂— | —CH₂— |
| CH₃ | H | H | CF₃ | —CH₂— | —CH₂— | —CH₂— | —CH₂— |
| CH(CH₃)₂ | CH₃ | H | H | —CH₂— | —CH₂— | —CH₂— | —CH₂— |
| CH(CH₃)₂ | H | CH₃ | H | —CH₂— | —CH₂— | —CH₂— | —CH₂— |
| CH(CH₃)₂ | H | H | CH₃ | —CH₂— | —CH₂— | —CH₂— | —CH₂— |
| CH(CH₃)₂ | OCH₃ | H | H | —CH₂— | —CH₂— | —CH₂— | —CH₂— |
| CH(CH₃)₂ | H | OCH₃ | H | —CH₂— | —CH₂— | —CH₂— | —CH₂— |
| CH(CH₃)₂ | H | H | OCH₃ | —CH₂— | —CH₂— | —CH₂— | —CH₂— |
| CH(CH₃)₂ | Cl | H | H | —CH₂— | —CH₂— | —CH₂— | —CH₂— |
| CH(CH₃)₂ | H | Cl | H | —CH₂— | —CH₂— | —CH₂— | —CH₂— |
| CH(CH₃)₂ | H | H | Cl | —CH₂— | —CH₂— | —CH₂— | —CH₂— |
| CH(CH₃)₂ | F | H | H | —CH₂— | —CH₂— | —CH₂— | —CH₂— |
| CH(CH₃)₂ | H | F | H | —CH₂— | —CH₂— | —CH₂— | —CH₂— |
| CH(CH₃)₂ | H | H | F | —CH₂— | —CH₂— | —CH₂— | —CH₂— |
| CH(CH₃)₂ | CF₃ | H | H | —CH₂— | —CH₂— | —CH₂— | —CH₂— |
| CH(CH₃)₂ | H | CF₃ | H | —CH₂— | —CH₂— | —CH₂— | —CH₂— |
| CH(CH₃)₂ | H | H | CF₃ | —CH₂— | —CH₂— | —CH₂— | —CH₂— |
| CH₂Ph | CH₃ | H | H | —CH₂— | —CH₂— | —CH₂— | —CH₂— |
| CH₂Ph | H | CH₃ | H | —CH₂— | —CH₂— | —CH₂— | —CH₂— |
| CH₂Ph | H | H | CH₃ | —CH₂— | —CH₂— | —CH₂— | —CH₂— |
| CH₂Ph | OCH₃ | H | H | —CH₂— | —CH₂— | —CH₂— | —CH₂— |
| CH₂Ph | H | OCH₃ | H | —CH₂— | —CH₂— | —CH₂— | —CH₂— |
| CH₂Ph | H | H | OCH₃ | —CH₂— | —CH₂— | —CH₂— | —CH₂— |
| CH₂Ph | Cl | H | H | —CH₂— | —CH₂— | —CH₂— | —CH₂— |
| CH₂Ph | H | Cl | H | —CH₂— | —CH₂— | —CH₂— | —CH₂— |
| CH₂Ph | H | H | Cl | —CH₂— | —CH₂— | —CH₂— | —CH₂— |
| CH₂Ph | F | H | H | —CH₂— | —CH₂— | —CH₂— | —CH₂— |
| CH₂Ph | H | F | H | —CH₂— | —CH₂— | —CH₂— | —CH₂— |
| CH₂Ph | H | H | F | —CH₂— | —CH₂— | —CH₂— | —CH₂— |
| CH₂Ph | CF₃ | H | H | —CH₂— | —CH₂— | —CH₂— | —CH₂— |
| CH₂Ph | H | CF₃ | H | —CH₂— | —CH₂— | —CH₂— | —CH₂— |
| CH₂Ph | H | H | CF₃ | —CH₂— | —CH₂— | —CH₂— | —CH₂— |
| CH₂CH₂OCH₃ | CH₃ | H | H | —CH₂— | —CH₂— | —CH₂— | —CH₂— |
| CH₂CH₂OCH₃ | H | CH₃ | H | —CH₂— | —CH₂— | —CH₂— | —CH₂— |
| CH₂CH₂OCH₃ | H | H | CH₃ | —CH₂— | —CH₂— | —CH₂— | —CH₂— |
| CH₂CH₂OCH₃ | OCH₃ | H | H | —CH₂— | —CH₂— | —CH₂— | —CH₂— |
| CH₂CH₂OCH₃ | H | OCH₃ | H | —CH₂— | —CH₂— | —CH₂— | —CH₂— |
| CH₂CH₂OCH₃ | H | H | OCH₃ | —CH₂— | —CH₂— | —CH₂— | —CH₂— |
| CH₂CH₂OCH₃ | Cl | H | H | —CH₂— | —CH₂— | —CH₂— | —CH₂— |
| CH₂CH₂OCH₃ | H | Cl | H | —CH₂— | —CH₂— | —CH₂— | —CH₂— |
| CH₂CH₂OCH₃ | H | H | Cl | —CH₂— | —CH₂— | —CH₂— | —CH₂— |
| CH₂CH₂OCH₃ | F | H | H | —CH₂— | —CH₂— | —CH₂— | —CH₂— |
| CH₂CH₂OCH₃ | H | F | H | —CH₂— | —CH₂— | —CH₂— | —CH₂— |
| CH₂CH₂OCH₃ | H | H | F | —CH₂— | —CH₂— | —CH₂— | —CH₂— |
| CH₂CH₂OCH₃ | CF₃ | H | H | —CH₂— | —CH₂— | —CH₂— | —CH₂— |
| CH₂CH₂OCH₃ | H | CF₃ | H | —CH₂— | —CH₂— | —CH₂— | —CH₂— |
| CH₂CH₂OCH₃ | H | H | CF₃ | —CH₂— | —CH₂— | —CH₂— | —CH₂— |
| H | H | H | H | —CH(CH₃)— | —CH₂— | —CH₂— | —CH₂— |

TABLE 2-continued

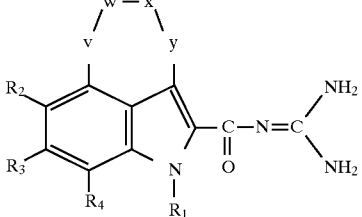

| R1 | R2 | R3 | R4 | -v- | -w- | -x- | -y- |
|---|---|---|---|---|---|---|---|
| CH₃ | H | H | H | —CH(CH₃)— | —CH₂— | —CH₂— | —CH₂— |
| CH(CH₃)₂ | H | H | H | —CH(CH₃)— | —CH₂— | —CH₂— | —CH₂— |
| CH₂Ph | H | H | H | —CH(CH₃)— | —CH₂— | —CH₂— | —CH₂— |
| CH₂CH₂OCH₃ | H | H | H | —CH(CH₃)— | —CH₂— | —CH₂— | —CH₂— |
| H | H | H | H | —CO— | —CH₂— | —CH₂— | —CH₂— |
| CH₃ | H | H | H | —CO— | —CH₂— | —CH₂— | —CH₂— |
| CH(CH₃)₂ | H | H | H | —CO— | —CH₂— | —CH₂— | —CH₂— |
| CH₂Ph | H | H | H | —CO— | —CH₂— | —CH₂— | —CH₂— |
| CH₂CH₂OCH₃ | H | H | H | —CO— | —CH₂— | —CH₂— | —CH₂— |
| H | F | H | H | —C(=CH₂)— | —CH₂— | —CH₂— | —CH₂— |
| CH₃ | H | F | H | —C(=CH₂)— | —CH₂— | —CH₂— | —CH₂— |
| CH(CH₃)₂ | H | H | F | —C(=CH₂)— | —CH₂— | —CH₂— | —CH₂— |
| CH₂Ph | CF₃ | H | H | —C(=CH₂)— | —CH₂— | —CH₂— | —CH₂— |
| CH₂CH₂OCH₃ | H | CF₃ | H | —C(=CH₂)— | —CH₂— | —CH₂— | —CH₂— |

| R1 | R2 | R3 | R4 | -v-w- | -x- | -y- |
|---|---|---|---|---|---|---|
| H | H | H | H | —CH=CH— | —CH₂— | —CH₂— |
| CH₃ | H | H | H | —CH=CH— | —CH₂— | —CH₂— |
| CH(CH₃)₂ | H | H | H | —CH=CH— | —CH₂— | —CH₂— |
| CH₂Ph | H | H | H | —CH=CH— | —CH₂— | —CH₂— |
| CH₂CH₂OCH₃ | H | H | H | —CH=CH— | —CH₂— | —CH₂— |

| R1 | R2 | R3 | R4 | -v- | -w- | -x-y- |
|---|---|---|---|---|---|---|
| H | H | H | H | —CH₂— | —CH₂— | —CH=CH— |
| CH₃ | H | H | H | —CH₂— | —CH₂— | —CH=CH— |
| CH(CH₃)₂ | H | H | H | —CH₂— | —CH₂— | —CH=CH— |
| CH₂Ph | H | H | H | —CH₂— | —CH₂— | —CH=CH— |
| CH₂CH₂OCH₃ | H | H | H | —CH₂— | —CH₂— | —CH=CH— |

| R1 | R2 | R3 | R4 | -v- | -w- | -w- | -x- |
|---|---|---|---|---|---|---|---|
| H | H | H | H | —CH₂— | —CH₂— | —CH₂— | —CO— |
| CH₃ | H | H | H | —CH₂— | —CH₂— | —CH₂— | —CO— |
| CH(CH₃)₂ | H | H | H | —CH₂— | —CH₂— | —CH₂— | —CO— |
| CH₂Ph | H | H | H | —CH₂— | —CH₂— | —CH₂— | —CO— |
| CH₂CH₂OCH₃ | H | H | H | —CH₂— | —CH₂— | —CH₂— | —CO— |
| H | H | H | H | —CH₂— | —CH₂— | —CH₂— | —C(=CH₂)— |
| CH₃ | H | H | H | —CH₂— | —CH₂— | —CH₂— | —C(=CH₂)— |
| CH(CH₃)₂ | H | H | H | —CH₂— | —CH₂— | —CH₂— | —C(=CH₂)— |
| CH₂Ph | H | H | H | —CH₂— | —CH₂— | —CH₂— | —C(=CH₂)— |
| CH₂CH₂OCH₃ | H | H | H | —CH₂— | —CH₂— | —CH₂— | —C(=CH₂)— |
| H | F | H | H | —CH₂— | —CH₂— | —CH₂— | —CH(CH₃)— |
| CH₃ | H | F | H | —CH₂— | —CH₂— | —CH₂— | —CH(CH₃)— |
| CH(CH₃)₂ | H | H | F | —CH₂— | —CH₂— | —CH₂— | —CH(CH₃)— |
| CH₂Ph | CF₃ | H | H | —CH₂— | —CH₂— | —CH₂— | —CH(CH₃)— |
| CH₂CH₂OCH₃ | H | CF₃ | H | —CH₂— | —CH₂— | —CH₂— | —CH(CH₃)— |

The substituted guanidine derivative of the present invention has the guanidino moiety shown in the above formula (1) and has tautomers. In detail, there are a tautomer [Ind-C(O)N=C(NH₂)₂] whose guanidino moiety is diaminomethyleneamino, and another tautomer [Ind-C(O)NH—C(=NH)NH₂] whose guanidino moiety is aminoiminomethylamino (in the above formulas, Ind is an indole moiety). These tautomers are different only in state and are the same compound. Therefore, the present invention includes both of the tautomers.

The compound of the general formula (1) includes those having an optical center of asymmetry. The compound having an optical center of asymmetry may be obtained as a racemic modification, or it may be obtained as an optically active substance when an optically active starting material is used. If necessary, the racemic modification obtained may be physically or chemically resolved into optical antipodes by a conventional method. Preferably, diastereomers are formed from the racemic modification by a reaction using a reagent for optical resolution. The diastereomers different in form may be resolved by a conventional method such as fractional crystallization.

If necessary, the compound of the general formula (1) may be converted to a pharmaceutically acceptable addition salt with an inorganic acid or an organic acid. As such an acid addition salt, there may be exemplified salts with mineral acids such as hydrochloric acid, hydrobromic acid, sulfuric acid, phosphoric acid, etc.; salts with organic carboxylic acids such as formic acid, acetic acid, fumaric acid, maleic acid, oxalic acid, citric acid, malic acid, tartaric acid, aspartic acid, glutamic acid, etc.; and salts with sulfonic acids such as methanesulfonic acid, benzenesulfonic acid, p-toluenesulfonic acid, hydroxybenzenesulfonic acid, dihydroxybenzenesulfonic acid, etc.

Each of the compounds of the general formula (1) and the acid addition salts thereof may be in the form of an anhydride, hydrate or solvate.

The compounds of the present invention inhibit the sodium/proton ($Na^+/H^+$) exchange transport system and hence are useful as a therapeutic or prophylactic agent for diseases caused by a trouble with the sodium/proton ($Na^+/H^+$) exchange transport system, for example, hypertension, organ disorders associated with ischemia or ischemic reperfusion, arrhythmia, angina pectoris, diabetes mellitus, cardiac hypertrophy, cerebro-ischemic disorders, diseases caused by excessive cell proliferations, or diseases caused by endothelial cell injury.

When used as a therapeutic or prophylactic agent, the compound of the present invention may be orally or parenterally administered. That is, the compound may be orally administered in a usual dosage form such as powder, granules, tablets, capsules, syrup, suspension or the like, or it may be parenterally administered, for example, by injection of a solution, emulsion or suspension prepared from the compound. The compound may be administered rectally in the form of a suppository. The compound of the present invention may be formulated into the above-exemplified suitable dosage form by blending the compound as active ingredient with conventional acceptable adjuvants such as a carrier, excipient, binder, stabilizer, diluent, etc. When the compound is used in the form of an injection, the injection may contain pharmaceutically acceptable additives such as a buffer, solubilizer, tonicity agent, etc. Although the dose and the number of administrations are varied depending on, for example, a disease to be cured, the condition of the disease, age, body weight and administration route, the compound may be administered to an adult in a dose of usually 0.1 to 2,000 mg, preferably 1 to 200 mg per day in one portion or several portions.

The present invention is more concretely illustrated with the following reference examples, examples and test example, which should not be construed as limiting the scope of the invention.

REFERENCE EXAMPLE 1

Synthesis of ethyl 1,3,4,5-tetrahydro-1-methyl-benz[cd]indole-2-carboxylate

To a solution of ethyl 1,3,4,5-tetrahydro-benz[cd] indole-2-carboxylate (1.00 g, 4.36 mmol) in N,N-dimethylformamide (20 ml) was added 60% sodium hydride (0.19 g, 4.80 mmol), followed by stirring at room temperature for 30 minutes. Then, methyl iodide (1.86 g, 13.1 mmol) was added and the resulting mixture was stirred at room temperature for 2 hours, after which the reaction mixture was poured into ice water, followed by extraction with ethyl acetate (twice). The extract solution was washed with a 5% aqueous sodium chloride solution and then dried over anhydrous magnesium sulfate. The solvent was distilled off under reduced pressure and the residue was purified by a silica gel column chromatography (eluent: ethyl acetate/n-hexane=1.5/98.5) to obtain ethyl 1,3,4,5-tetrahydro-1-methyl-benz[cd]indole-2-carboxylate (1.03 g).

Melting point: 80°–81° C. (after recrystallization from isopropanol).

The following compounds were synthesized according to the process described in Reference Example 1:
(1) Ethyl 1,3,4,5-tetrahydro-1-methyl-5-oxo-benz[cd]indole-2-carboxylate Melting point: 111°–112° C. (after recrystallization from isopropanol),
(2) Ethyl 3,4,5,6-tetrahydro-1-methyl-6-oxo-1H-cyclohepta[cd]indole-2-carboxylate Melting point: 109°–110° C. (after recrystallization from isopropanol), and
(3) Methyl 1,3,4,5-tetrahydro-7-chloro-1-methyl-benz[cd]indole-2-carboxylate Melting point: 136°–137° C. (after recrystallization from isopropanol).

REFERENCE EXAMPLE 2

Synthesis of ethyl 1,3,4,5-tetrahydro-5-hydroxy-benz[cd]indole-2-carboxylate

A mixture of ethyl 1,3,4,5-tetrahydro-5-oxo-benz[cd] indole-2-carboxylate (0.40 g, 1.64 mmol), sodium borohydride (0.062 g, 1.64 mmol), ethanol (2 ml) and tetrahydrofuran (8 ml) was stirred at 0°–5° C. for 1.5 hours. The reaction mixture was poured into a 5% aqueous sodium chloride solution, followed by extraction with ethyl acetate (three times). The extract solution was washed twice with a 5% aqueous sodium chloride solution and then dried over anhydrous magnesium sulfate. The solvent was distilled off under reduced pressure and the residue was purified by a silica gel column chromatography (eluent: ethyl acetate/n-hexane=15/85) to obtain ethyl 1,3,4,5-tetrahydro-5-hydroxy-benz[cd]indole-2-carboxylate (0.40 g).

Melting point: 166°–170° C. (decompose) (after recrystallization from toluene).

The following compounds were synthesized according to the process described in Reference Example 2:
(1) Ethyl 3,4,5,6-tetrahydro-6-hydroxy-1H-cyclo-hepta[cd]indole-2-carboxylate Melting point: 136°–138° C. (after recrystallization from toluene), (2) Ethyl 1,3,4,5-tetrahydro-5-hydroxy-1-methyl-benz[cd]indole-2-carboxylate Melting point: 102°–103° C. (after recrystallization from toluene/n-hexane), and
(3) Ethyl 3,4,5,6-tetrahydro-6-hydroxy-1-methyl-1H-cyclohepta[cd]indole-2-carboxylate Melting point: 88°–89° C. (after recrystallization from toluene/n-hexane),

REFERENCE EXAMPLE 3

Synthesis of ethyl 1,3,4,5-tetrahydro-5-methoxy-1-methyl-benz[cd] indole-2-carboxylate Ethyl 1,3,4,5-tetrahydro-5-hydroxy-1-methyl-benz[cd] indole-2-carboxylate (0.25 g, 0.96 mmol) was added to a suspension of 60% sodium hydride (0.039 g, 0.96 mmol) in tetrahydrofuran (10 ml), followed by stirring at room temperature for 20 minutes. After the reaction mixture was cooled to 0°–5° C., methyl iodide (0.27 g, 1.93 mmol) was added thereto and the resulting mixture was stirred at 0°–5° C. for 1 hour and then at room temperature for 2.5 hours. The reaction mixture was poured into a 5% aqueous sodium chloride solution, followed by extraction with ethyl acetate (twice). The extract solution was washed twice with a 5% aqueous sodium chloride solution and then dried over anhydrous magnesium sulfate. The solvent was distilled off under reduced pressure and the residue was purified by a silica gel column chromatography (eluent: ethyl acetate/n-hexane=2/98) to obtain ethyl 1,3,4,5-tetrahydro-5-methoxy-1-methyl-benz[cd]indole-2-carboxylate (0.16 g).

Melting point: 63°–64° C. (after recrystallization from n-hexane).

The following compounds were synthesized according to the process described in Reference Example 3:
(1) Ethyl 3,4,5,6-tetrahydro-6-methoxy -1-methyl-1H-cyclohepta[cd]indole-2-carboxylate (oil)
$^1$Hnmr (CDCl$_3$) δ: 1.40–1.45(3H, m), 1.81–1.89(1H, m), 2.19–2.35(3H, m), 3.19–3.29(1H, m), 3.35(3H, s), 3.38–3.44(1H, m), 3.98(3H, s), 4.40(2H, dd, J=7.26,14.19 Hz), 4.55–4.57(1H, m), 7.12–7.15(1H, m), 7.26–7.34(2H, m).

REFERENCE EXAMPLE 4

Synthesis of ethyl 1,3,4,5-tetrahydro -1-benzyl-benz[cd]indole-2-carboxylate

Ethyl 1,3,4,5-tetrahydro-benz[cd]indole-2-carboxylate (0.40 g, 1.74 mmol) was added to a suspension of 60% sodium hydride (0.077 g, 1.92 mmol) in N,N-dimethylformamide (5 ml), followed by stirring at room temperature for 30 minutes. Then, benzyl bromide (0.36 g, 2.09 mmol) was added and the resulting mixture was stirred for 1.5 hours. Thereafter, the same after-treatment as in Reference Example 1 was carried out to obtain an oil of ethyl 1,3,4,5-tetrahydro -1benzyl-benz[cd]indole-2-carboxylate. $^1$Hnmr (CDCl$_3$) δ:
1.32–1.37(3H, m), 2.06–2.15(2H, m), 2.95(2H,t, J=5.94 Hz), 3.12–3.16(2H, m), 4.27–4.35((2H,m), 5.76(2H, s), 6.84 (1H, d, J=6.27 Hz), 7.06–7.11(3H, m), 7.17–7.27(4H, m).

The following synthesis was carried out according to the process described in Reference Example 4:
(1) Synthesis of ethyl 1,3,4,5-tetrahydro -1isopropyl-benz[cd]indole-2-carboxylate Ethyl 1,3,4,5-tetrahydro -1-isopropyl-benz[cd]indole-2-carboxylate was obtained by the same process as in Reference Example 4 except for using 2-iodopropane in place of benzyl bromide.

Melting point: 60°–63° C. (after recrystallization from n-hexane).

REFERENCE EXAMPLE 5

Synthesis of ethyl 3,4,5,6-tetrahydro -1-methyl-6-methylene-1H-cyclohepta[cd] indole-2-carboxylate To dimethyl sulfoxide (5 ml) was added 60% sodium hydride (0.13 g, 3.17 mmol), followed by stirring at 75° C. for 45 minutes. After the reaction mixture was cooled to room temperature, a solution of methyltriphenylphosphonium iodide (1.28 g, 3.17 mmol) in dimethyl sulfoxide (10 ml) was added thereto and the resulting mixture was stirred at 60° C. for 10 minutes. The reaction mixture was re-cooled to room temperature, after which ethyl 3,4,5,6-tetrahydro -1-methyl-6-oxo-1H-cyclohepta[cd]indole-2-carboxylate (0.86 g, 3.17 mmol) was added thereto and the resulting mixture was allowed to stand overnight at room temperature. The reaction mixture was poured into a 5% aqueous sodium chloride solution, followed by extraction with ethyl acetate (twice). The extract solution was washed twice with a 5% aqueous sodium chloride solution and then dried over anhydrous magnesium sulfate. The solvent was distilled off under reduced pressure and the residue was purified by a silica gel column chromatography (eluent: ethyl acetate/n-hexane=1/99) to obtain ethyl 3,4,5,6-tetrahydro-1-methyl-6-methylene-1-H-cyclohepta[cd]indole-2-carboxylate (0.36 g).

Melting point: 45°–49° C. (after recrystallization from isopropanol/n-hexane).

REFERENCE EXAMPLE 6

Synthesis of ethyl 3,4,5,6-tetrahydro-1-methyl-1H-cyclohepta[cd] indole-2-carboxylate A mixture of ethyl 3,4,5,6-tetrahydro -1-methyl-6-oxo-1H-cyclohepta[cd]indole-2-carboxylate (0.40 g, 1.47 mmol), trifluoroacetic acid (4 ml) and triethylsilane (Et3SiH) (0.69 g, 5.90 mmol) was stirred overnight at room temperature. The reaction mixture was concentrated under reduced pressure and a 5% aqueous sodium chloride solution was added to the residue, followed by extraction with ethyl acetate (twice). The extract solution was washed with a 5% aqueous sodium chloride solution and then dried over anhydrous magnesium sulfate. The solvent was distilled off under reduced pressure and the residue was purified by a silica gel column chromatography (eluent: ethyl acetate/n-hexane=1/99) to obtain an oil of 3,4,5,6-tetrahydro-1-methyl-1-H-cyclohepta[cd]indole-2-carboxylate.

$^1$Hnmr (CDCl3)δ: 1.40–1.46(3H, m), 2.00(4H, dd, J=2.97,6.27 Hz), 3.10–3.20(2H, m), 3.25–3.35(2H, m), 3.97 (3H, s), 4.41(2H, dd, J=7.26,14.19 Hz), 6.89(1H, dd, J=0.99, 6.60Hz), 7.15–7.23(2H, m).

EXAMPLE 1

Synthesis of N-(aminoiminomethyl)-1,3,4,5-tetrahydro-5-oxo-benz[cd]indole-2-carboxamide methanesulfonate

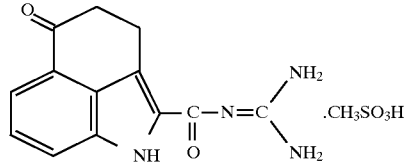

A mixture of ethyl 1,3,4,5-tetrahydro-5-oxo-benz[cd] indole-2-carboxylate (1.00 g, 4.11 mmol), sodium methoxide (2.22 g, 41.1 mmol), guanidine hydrochloride (3.92 g, 41.1 mmol) and N,N-dimethylformamide (15 ml) was stirred overnight at room temperature. After completion of the reaction, a 5% aqueous sodium chloride solution was added to the reaction mixture under ice-cooling, followed by extraction with ethyl acetate (three times). The extract solution was washed twice with a 5% aqueous sodium hydrogencarbonate solution and then dried over anhydrous magnesium sulfate. The solvent was distilled off under reduced pressure and the residue was purified by a silica gel column chromatography (eluent: chloroform/methanol=95/5) to obtain N-(aminoiminomethyl) -1,3,4,5-tetrahydro-5-oxo-benz[cd]indole-2-carboxamide (1.00 g). This compound (1.00 g) was treated with a mixture of isopropanol/water and methanesulfonic acid (0.75 g, 7.80 mmol) to obtain crude N-(aminoiminomethyl)-1,3,4,5-tetrahydro-5-oxo-benz[cd]indole-2-carboxamide methanesulfonate. This crude product was recrystallized from methanesulfonic acid (0.04 g, 0.39 mmol) and water (36 ml) to obtain N-(aminoiminomethyl)-1,3,4,5-tetrahydro-5-oxo-benz[cd] indole-2-carboxamide methanesulfonate (0.72 g).

Melting point: 240°–241° C. (decomp.).

EXAMPLE 2

Synthesis of N-(aminoiminomethyl)-1,3,4,5-tetrahydro-1-methyl-benz[cd]indole-2-carboxamide methanesulfonate

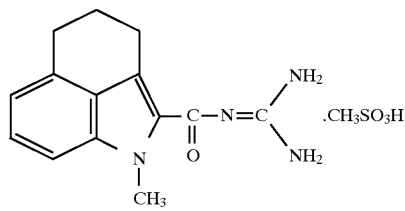

N-(aminoiminomethyl)-1,3,4,5-tetrahydro-1-methyl-benz[cd]indole-2-carboxamide methanesulfonate (0.24 g) was obtained by carrying out reaction according to the method described in Example 1, except for using ethyl 1,3,4,5-tetrahydro-1methyl-benz[cd]indole-2-carboxylate (0.37 g, 1.50 mmol), sodium methoxide (0.81 g, 15.0 mmol), guanidine hydrochloride (1.43 g, 15.0 mmol) and N,N-dimethylformamide (15 ml).

Melting point: 233°–234° C. (decomp.).

EXAMPLE 3

Synthesis of N-(aminoiminomethyl)-1,3,4,5-tetrahydro-benz[cd]indole-2-carboxamide methanesulfonate

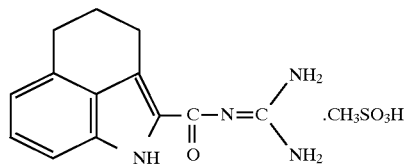

N-(aminoiminomethyl)-1,3,4,5-tetrahydro-benz[cd]indole-2-carboxamide methanesulfonate (0.18 g) was obtained by carrying out reaction according to the method described in Example 1, except for using ethyl 1,3,4,5-tetrahydro-benz[cd]indole-2-carboxylate (0.34 g, 1.50 mmol), sodium methoxide (0.81 g, 15.0 mmol), guanidine hydrochloride (1.43 g, 15.0 mmol) and N,N-dimethylformamide (15 ml).

Melting point: 253°–254° C. (decomp.).

The following compounds of Examples 4 to 15 were synthesized by carrying out reaction according to the method described in Example 1.

EXAMPLE 4

Synthesis of N-(aminoiminomethyl)-1,3,4,5-tetrahydro-1-methyl-5-oxo-benz[cd]indole-2-carboxamide methanesulfonate

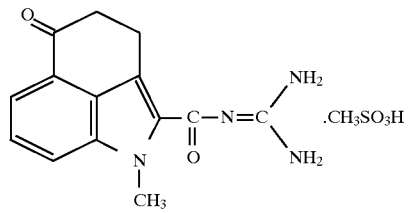

Melting point: 248°–249° C. (decomp.).

EXAMPLE 5

Synthesis of N-(aminoiminomethyl)-3,4,5,6-tetrahydro-6-oxo-1-H--cyclohepta[cd]indole-2-carboxamide methanesulfonate

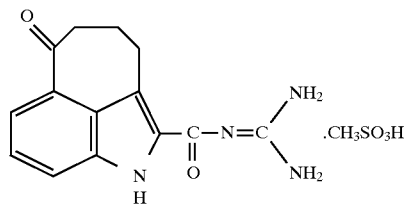

Melting point: 250°–251° C. (decomp.).

EXAMPLE 6

Synthesis of N-(aminoiminomethyl)-3,4,5,6-tetrahydro-1-methyl-6-oxo-1-H--cyclohepta[cd]indole-2-carboxamide methanesulfonate

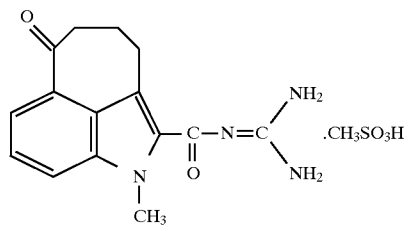

Melting point: 268°–269° C. (decomp.).

EXAMPLE 7

Synthesis of N-(aminoiminomethyl)-1,3,4,5-tetrahydro-5-hydroxy-benz[cd]indole-2-carboxamide methanesulfonate

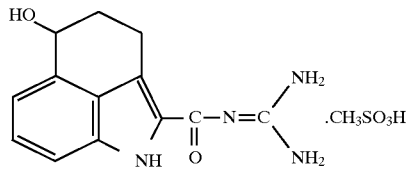

Melting point: 162°–163° C. (decomp.).

This compound was obtained by methanesulfonation using tetrahydrofuran as a solvent.

EXAMPLE 8

Synthesis of N-(aminoiminomethyl)-1,3,4,5-tetrahydro-5-hydroxy -1-methyl-benz[cd]indole-2-carboxamide methanesulfonate

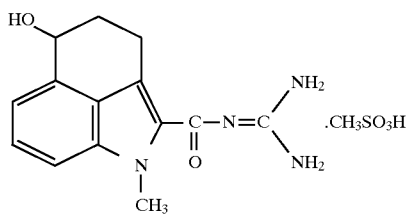

Melting point: 156°–157° C. (decomp.).

This compound was obtained by methanesulfonation using tetrahydrofuran as a solvent.

EXAMPLE 9

Synthesis of N-(aminoiminomethyl)-1,3,4,5-tetrahydro-5-methoxy -1-methyl-benz[cd]indole-2-carboxamide methanesulfonate

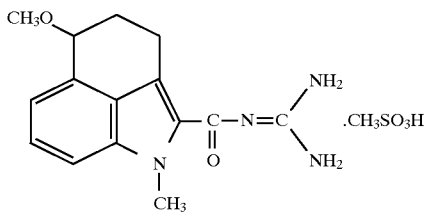

Melting point: 165°–166° C. (decomp.).

This compound was obtained by methanesulfonation using tetrahydrofuran as a solvent.

EXAMPLE 10

Synthesis of N-(aminoiminomethyl)-3,4,5,6-tetrahydro-6-methoxy -1-methyl-1-H--cyclohepta[cd]indole-2-carboxamide methanesulfonate

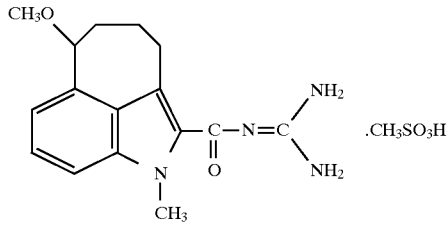

Melting point: 239°–240° C. (decomp.).

This compound was obtained by methanesulfonation using tetrahydrofuran as a solvent.

EXAMPLE 11

Synthesis of N-(aminoiminomethyl)-1,3,4,5-tetrahydro-7-chloro -1-methyl-benz[cd]indole-2-carboxamide methanesulfonate

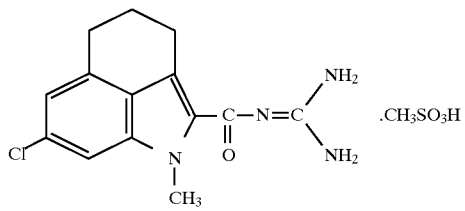

Melting point: 267°–268° C. (decomp.).

This compound was obtained by methanesulfonation using tetrahydrofuran as a solvent.

EXAMPLE 12

Synthesis of N-(aminoiminomethyl)-1,3,4,5-tetrahydro -1-benzyl-benz[cd]indole-2-carboxamide methanesulfonate

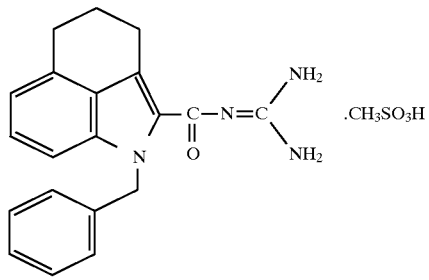

Melting point: 230°–231° C. (decomp.).

This compound was obtained by methanesulfonation using tetrahydrofuran as a solvent.

EXAMPLE 13

Synthesis of N-(aminoiminomethyl)-3,4,5,6-tetrahydro -1-methyl-6-methylene-1-H-cyclohepta[cd]indole-2-carboxamide methanesulfonate

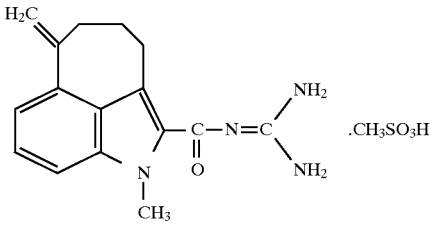

Melting point: 229°–230° C. (decomp.).

This compound was obtained by methanesulfonation using tetrahydrofuran as a solvent.

EXAMPLE 14

Synthesis of N-(aminoiminomethyl)-1,3,4,5-tetrahydro-1-isopropyl-benz[cd]indole-2-carboxamide methanesulfonate

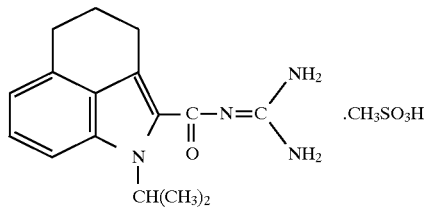

Melting point: 216°–218° C..

This compound was obtained by methanesulfonation using tetrahydrofuran as a solvent.

EXAMPLE 15

Synthesis of N-(aminoiminomethyl)-3,4,5,6-10-tetrahydro-1-methyl-1-H-cyclohepta[cd]indole-2-carboxamide methanesulfonate

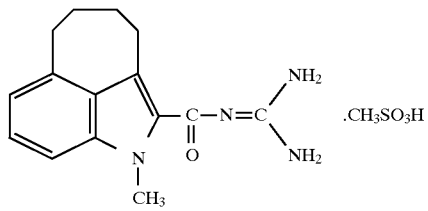

Melting point: 223°–224° C.

This compound was obtained by methanesulfonation using tetrahydrofuran as a solvent.

EXAMPLE 16

Synthesis of N-(aminoiminomethyl)-1,3,4,5-tetrahydro-5-methoxy-benz[cd]indole-2-carboxamide methanesulfonate

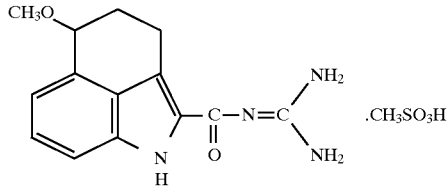

A mixture of the N-(aminoiminomethyl)-1,3,4,5-tetrahydro-5-hydroxy-benz[cd]indole-2-carboxamide methanesulfonate (0.13 g, 0.37 mmol) obtained in Example 7, methanesulfonic acid (0.036 g, 0.37 mmol) and methanol (20 ml) was heated under reflux for 2 hours. Subsequently, the reaction mixture was concentrated to a volume of about 5 ml under reduced pressure and a 5% aqueous sodium chloride solution was added to the residue. The resulting mixture was made basic with 28% aqueous ammonia and extracted twice with ethyl acetate, and the extract solution was washed twice with a 5% aqueous sodium chloride solution and then dried over anhydrous magnesium sulfate. The solvent was distilled off under reduced pressure and the residue was purified by a silica gel column chromatography (eluent: chloroform/methanol=96/4) to obtain N-(aminoiminomethyl)-1,3,4,5-tetrahydro-5-methoxy-benz[cd]indole -2-carboxamide (0.11 g). This compound (0.11 g) was treated with a solution of methanesulfonic acid (0.05 g) in tetrahydrofuran (2.5 ml) to obtain N-(aminoiminomethyl)-1,3,4,5-tetrahydro-5-methoxy-benz[cd]indole-2-carboxamide methanesulfonate (0.08 g).

Melting point: 174°–175° C. (decomp.).

EXAMPLE 17

Synthesis of N-(aminoiminomethyl)-3,4-dihydro-1H-cyclohepta[cd]indole-2-carboxamide methanesulfonate

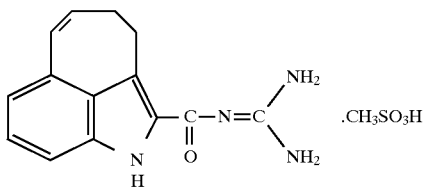

A mixture of ethyl 3,4,5,6-tetrahydro-6-hydroxy-1-H-cyclohepta[cd]indole-2-carboxylate (0.30 g, 1.16 mmol), sodium methoxide (1.26 g, 23.1 mmol), guanidine hydrochloride (2.22 g, 23.1 mmol) and N,N-dimethylformamide (15 ml) was stirred at room temperature for 3 days. The reaction mixture was poured into a 5% aqueous sodium chloride solution, followed by extraction with ethyl acetate (three times). The extract solution was washed twice with a 5% aqueous sodium chloride solution and then dried over anhydrous magnesium sulfate. The solvent was distilled off under reduced pressure to obtain crude N-(aminoiminomethyl)-3,4,5,6-tetrahydro-6-hydroxy-1H-cyclohepta [cd]indole-2carboxamide. This crude product was added to a solution of methanesulfonic acid (0.22 g) in tetrahydrofuran (12 ml) and the resulting mixture was stirred at 0°–5° C. The insoluble materials were filtered off and the filtrate was concentrated under reduced pressure. A 5% aqueous sodium chloride solution was added to the thus obtained residue, and the resulting mixture was made basic with 28% aqueous ammonia and extracted twice with ethyl acetate. The extract solution was washed with a 5% aqueous sodium chloride solution and then dried over anhydrous magnesium sulfate. The solvent was distilled off under reduced pressure and the residue was purified by a silica gel column chromatography (eluent: chloroform/methanol=96/4) to obtain N-(aminoiminomethyl)-3,4-dihydro-1H-cyclohepta[cd]indole-2-carboxamide (0.16 g). This compound (0.16 g) was treated with a solution of methanesulfonic acid (0.15 g) in tetrahydrofuran (3.5 ml) to obtain N-(aminoiminomethyl)-3,4-dihydro-1H-cyclohepta[cd]indole-2-carboxamide methanesulfonate (0.11 g).

Melting point: 264°–265° C. (decomp.).

The following compound of Example 18 was synthesized by carrying out reaction according to the method described in Example 17.

EXAMPLE 18

Synthesis of N-(aminoiminomethyl)-3,4-dihydro-1-methyl-1H-cyclohepta[cd]indole-2-carboxamide methanesulfonate

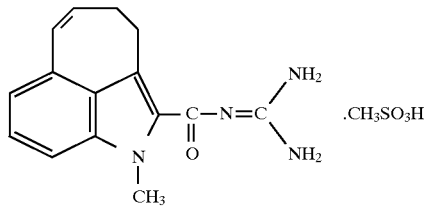

Melting point: 239°–240° C. (decomp.).

Test Example

Inhibitory effect on the Na+/H+ exchange transport system (in vitro)

Test Method

The test was carried out according to the method of Yamori et al. (J. Hypertension, 8, 153 (1990)). In detail, inhibitory effect on the Na+/H+ exchange transport system was evaluated by the change in intracellular pH during acid loading, using the vascular smooth muscle cells isolated from the rat thoracic aorta.

Test results

The obtained results are shown in Table 3 below.

TABLE 3

| Example | Inhibitory effect on $Na^+/H^+$ exchange transport system IC50 ($\mu M$) |
|---|---|
| 1 | 4.00 |
| 2 | 0.15 |
| 3 | 0.70 |

The compounds of the present invention inhibit the sodium/proton ($Na^+/H^+$) exchange transport system and hence are useful as a therapeutic or prophylactic agent for diseases caused by the acceleration of the sodium/proton ($Na^+/H^+$) exchange transport system, for example, hypertension, arrhythmia, angina pectoris, cardiac hypertrophy, diabetes mellitus, organ disorders associated with ischemia or ischemic reperfusion [e.g. heart muscle ischemic reperfusion-associated disorders, acute renal failute, or disorders induced by surgical treatment such as organ transplantation or percutaneous transluminal coronary angioplasty (PTCA)], cerebroischemic disorders [e.g. disorders associated with cerebral infarction, disorders caused after cerebral apoplexy as sequelae, or cerebral edema], diseases caused by excessive cell proliferation such as proliferation of fibroblast, proliferation of smooth muscle cells or proliferation of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or recurrent stricture after PTCA, or diseases caused by endothelial cell injury.

What we claim is:

1. A compound of formula (1):

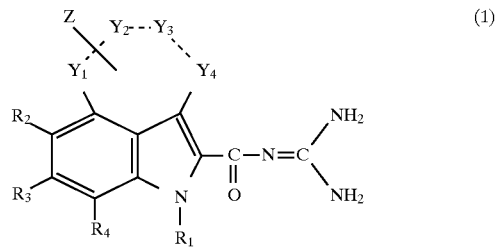

wherein $R_1$ is a hydrogen atom, an unsubstituted alkyl group, a substituted alkyl group, a cycloalkyl group, a cycloalkenyl group, a saturated heterocyclic group, an aromatic group, —$OR_5$, an acyl aromatic group, —Q—$R_a$;

$R_2$, $R_3$ and $R_4$ are independently a hydrogen atom, an unsubstituted alkyl group, a substituted alkyl group, a cycloalkyl group, a cycloalkenyl group, a saturated heterocyclic group, a halogen atom, a nitro group, a carboxyl group, an alkoxycarbonyl group, an aromatic group, —$OR_5$, —$N(R_6)R_7$, —$CON(R_6)R_7$, —$SO_2N(R_6)R_7$, —$S(O)_nR_8$, an acyl group, —Q—$R_a$ or

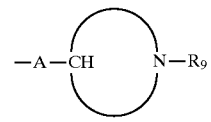

wherein the ring is a 3- to 8-membered saturated heterocyclic group composed of a nitrogen atom and carbon atoms;

$Y_1$, $Y_2$, $Y_3$ and $Y_4$ are as follows: (1) one of them is a methylene group, a carbonyl group, or —C(=C($R_{11}$)($R_{12}$))—, two others are independently a methylene group, and the remaining one is a single bond or a methylene group, or (2) any adjacent two members of a group consisting of $Y_1$, $Y_2$, $Y_3$ and $Y_4$ are taken together to represent a vinylene group, another is a methylene group, a carbonyl group, or —C(=C($R_{11}$)($R_{12}$))—, and the remaining one is a single bond or a methylene group;

Z is a substituent which may be substituted for at least on hydrogen atom bonded to any of the carbon atoms constituting the ring formed by $Y_1$, $Y_2$, $Y_3$ and $Y_4$, namely, Z may be absent, or one or more Zs may be present and are independently a substituent selected from the group consisting of unsubstitued alkyl groups, substituted alkyl groups, alkenyl groups, alkynyl groups, cycloalkyl groups, cycloalkenyl groups, saturated heterocyclic groups, halogen atoms, carboxyl group, alkoxycarbonyl groups, aromatic groups, —$OR_5$, —$N(R_6)R_7$, —$CON(R_6)R_7$, —$S(O)_nR_8$, acyl groups, and —Q—$R_a$;

A is an oxygen atom, —$S(O)_n$— or —$N(R)_{10}$—;

Q is an substituted or unsubstituted lower alkylene group;

$R_a$ is a substituted or unsubstituted vinyl group, or a substituted or unsubstituted ethynyl group;

$R_5$ is a hydrogen atom, an unsubstituted alkyl group, a substituted alkyl group, a cycloalkyl group, a cycloalkenyl group, a saturated heterocyclic group or an aromatic group;

$R_6$ and $R_7$ are independently a hydrogen atom, an unsubstituted alkyl group, a substituted alkyl group, a cycloalkyl group, a cycloalkenyl group, a saturated heterocyclic group, an aromatic group, an acyl group or —Q—$R_a$, or $R_6$ and $R_7$, when taken together with the nitrogen atom to which they are bonded, form a saturated 5- to 7-membered cyclic amino group which may contain an oxygen atom or sulfur atom in the ring or form a 5- to 7-membered cyclic group containing 1 to 3 nitrogen atoms, and may be substituted by one or two unsubstituted alkyl groups, substituted alkyl groups, hydroxyl groups or —$OR_5$ groups;

$R_8$ is an unsubstituted alkyl group, a substituted alkyl group or an aromatic group;

$R_9$ is a hydrogen atom, an unsubstituted alkyl group, a substituted alkyl group, an acyl group or —Q—$R_a$;

$R_{10}$ is a hydrogen atom, an unsubstituted alkyl group, a substituted alkyl group, a cycloalkyl group, a saturated heterocyclic group, an aromatic group, an acyl group or —Q—$R_a$;

$R_{11}$ and $R_{12}$ are independently a hydrogen atom, an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, —$OR_5$, —$N(R_6)R_7$, —CON($R_6$)$R_7$, —$S(O)_nR_8$, an acyl group or —Q—$R_a$; and n is 0, 1 or 2, or a pharmaceutically acceptable acid addition salt thereof, wherein:

said alkyl groups are, independently, linear or branched alkyl groups of 8 or less carbon atoms;

said cycloalkyl groups are, independently, 3- to 8-membered cycloalkyl groups and are unsubstituted or are substituted with 1 to 4 groups selected from the group consisting of unsubstituted alkyl groups, substituted alkyl groups, hydroxyl groups and —$OR_5$;

said cycloalkenyl groups are, independently, 3- to 8-membered cycloalkenyl groups and are unsubstituted or are substituted with 1 or 4 selected from the group consisting of unsubstituted alkyl groups, substituted alkyl groups, hydroxyl groups and —$OR_5$;

said saturated heterocyclic groups are, independently, 3- to 8-membered saturated heterocyclic groups having an oxygen atom or a sulfur atom and are unsubstituted or are substituted with 1 or 4 selected from the group consisting of unsubstituted alkyl groups, substituted alkyl groups, hydroxyl groups and —$OR_5$;

said alkoxycarbonyl groups are, independently, linear or branched alkoxycarbonyl groups of 6 or less carbon atoms;

said aromatic groups are, independently, substituted or unsubstituted aryl groups or substituted or unsubstituted heteroaryl groups;

said aryl groups are, independently, aryl groups of 10 or less carbon atoms;

said heteroaryl groups are, independently, 5- or 6-membered heteroaryl groups containing 1 to 4 nitrogen atoms or 5- or 6-membered heteroaryl groups containing 0 to 2 nitrogen atoms and an oxygen atom or a sulfur atom;

said substituents of the substituted aryl groups and the substituted heteroaryl groups are, independently, selected from the group consisting of unsubstituted alkyl group, substituted alkyl group, halogen atom, nitro group, alkoxycarbonyl group, carboxyl group, —$OR_5$, —$NR_6R_7$, $CONR_6R_7$, —$SO_2NR_6R_7$ and —$S(O)_nR_8$, said alkoxy groups are, independently, linear or branched alkoxy groups or 6 or less carbon atoms;

said substituents of the substituted alkyl groups are, independently, selected from the group consisting of halogen atom, hydroxyl group, alkoxy group, cycloalkyl group, cyano group, carboxyl group, alkoxy-carbonyl group, aromatic group, acyl group, —$CONR_pR_q$ wherein $R_p$ and $R_q$ are independently a hydrogen atom or an alkyl group, or $R_p$ and $R_q$, when taken together with the nitrogen atom to which they are bonded, form a saturaated 5-to 7-membered cyclic amino group which may contain an oxygen atom or a sulfur atom in the ring or form a 5- to 7-membered cyclic group containing 1 to 3 nitrogen atoms, and may be substituted by one or two unsubstituted alkyl groups, substituted alkyl groups, hydroxyl groups or —$OR_5$ groups, —$NR_6R_7$, and the formula:

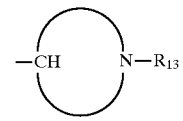

wherein $R_{13}$ is a hydrogen atom, an unsubstitued alkyl group or a substituted alkyl group and the ring is a 3- to 8-membered saturated heterocyclic ring containing a nitrogen atom;

said lower alkylene groups are, independently, alkylene groups of 6 or less carbon atoms;

said substituent on the lower alkylene group for Q and the substituent on the vinyl or ethynyl group for $R_a$ are, independently, selected from the group consisting of unsubstituted alkyl group, substituted alkyl group, cycloalkyl group, cycloalkenyl group, saturated heterocyclic group, carboxyl group, alkoxycarbonyl group, aromatic group, and —$CON(R_6)R_7$, said acyl groups are, independently, formyl groups, alkanoyl groups of 2 to 6 carbon atoms, cycloalkanecarbonyl groups of 3 to 6 carbon atoms, cycloakenecarbonyl groups of 3 to 6 carbon atoms, aroyl groups of 6 to 10 carbon atoms, saturated heterocyclic ring-carbonyl groups having a 5- or 6-membered saturated heterocyclic ring containing one or two heteroatoms selected from the group consisting of nitrogen atoms, oxygen atom and sulfur atoms, or heteroaromatic acyl groups have a 5- or 6-membered heteoaromatic ring containing one or two heteroatoms selected from the group consisting of nitrogen atom, oxygen atom and sulfur atom, said alkenyl groups are, independently, alkenyl groups of 6 or less carbon atoms; and said alkynyl groups are, independently, alkynyl group of 6 or less carbon atoms.

2. A compound according to claim 1, wherein $R_2$, $R_3$ and $R_4$ are independently a hydrogen atom, an unsubstituted alkyl group, a substituted alkyl group, a halogen atom, a nitro group, an aromatic group, —$OR_5$, —$N(R_6)R_7$, —$CON(R_6)R_7$, —$SO_2N(R_6)R_7$, —$S(O)_nR_8$, an acyl group or —Q—Ra wherein Ra is a substituted or unsubstituted vinyl group.

3. A compound according to claim 1 or 2, wherein one of $Y_1$, $Y_2$, $Y_3$ and $Y_4$ is a methylene group, a carbonyl group, or —$C(=C(R_{11})(R_{12}))$—, two others are independently a methylene group, and the remaining one is a single bond or a methylene group; and Z is as defined in claim 1.

4. A compound according to claim 1 or 2, wherein any adjacent two members of a group consisting of $Y_1$, $Y_2$, $Y_3$ and $Y_4$ are taken together to represent a substituted or unsubstituted vinylene group, another is a methylene group, a carbonyl group, or —$C(=C(R_{11})(R_{12}))$—, and the remaining one is a single bond or a methylene group; and Z is as defined in claim 1.

5. A compound according to claim 1 or 2, wherein $Y_1$ and $Y_2$ are taken together to represent a vinylene group, one of $Y_3$ and $Y_4$ is a methylene group, a carbonyl group, or —$C(=C(R_{11})(R_{12}))$— while the other is a single bond or a methylene group, and Z is as defined in claim 1.

6. A compound according to claim 1 or 2, wherein $Y_2$ and $Y_3$ are taken together to represent a vinylene group, one of $Y_1$ and $Y_4$ is a methylene group, a carbonyl group, or —$C(=C(R_{11})(R_{12}))$— while the other is a methylene group, and Z is as defined in claim 1.

7. A compound according to claim 1 or 2, wherein $Y_3$ and $Y_4$ are taken together to represent a vinylene group, one of $Y_1$ and $Y_2$ is a methylene group, a carbonyl group, or —$C(=C(R_{11})(R_{12}))$— while the other is a single bond or a methylene group, and Z is as defined in claim 1.

8. A compound according to claim 1 or 2, wherein one of $Y_1$, $Y_2$, $Y_3$ and $Y_4$ is a methylene group, a carbonyl group, or —$C(=C(R_{11})(R_{12}))$—, two others are independently a methylene group, and the remaining one is a single bond; and Z is as defined in claim 1.

9. A compound according to claim 1 or 2, wherein $Y_1$ is a carbonyl group, a methylene group or a vinylidene group, $Y_2$ and $Y_3$ are independently a methylene group, $Y_4$ is a single bond or a methylene group, and Z is a hydroxyl group or an alkoxy group.

10. A process for producing a compound according to claim 1, which comprises reacting a compound represented by the general formula:

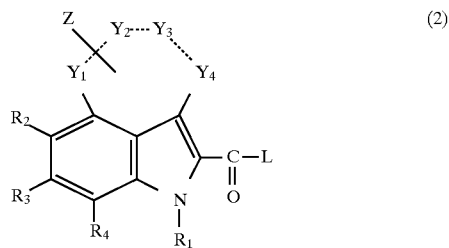

wherein $R_1$, $R_2$, $R_3$, $R_4$, $Y_1$, $Y_2$, $Y_3$ and $Y_4$ are as defined in claim 1, and L is a leaving group replaceable by a nucleophilic reagent, with guanidine.

11. A pharmaceutical composition comprising a compound according to claim 1 or 2 as an active ingredient.

12. A sodium/proton exchange transport system inhibitor comprising a compound according to claim 1 or 2 as an active ingredient.

13. A pharmaceutical composition for hypertension, arrhythmia, angina pectoris, cardiac hypertrophy, diabetes mellitus, organ disorders associated with ischemia or ischemic reperfusion, cerebro-ischemic disorders, diseases caused by excessive cell proliferation, or diseases caused by endothelial cell injury, which comprises a compound according to claim 1 or 2 as an active ingredient.

14. A method for inhibiting a sodium/proton exchange transport system which comprises administering to a mammal a compound according to claim 1 or 2 in a pharmaceutically effective amount.

15. A method for treating or preventing hypertension, arrhythmia, angina pectoris, cardiac hypertrophy, diabetes mellitus, organ disorders associated with ischemia or ischemic reperfusion, cerebro-isochemic disorders, diseases caused by excessive cell proliferation, or diseases caused by endothelial cell injury, which comprises administering to a mammal a compound according to claim 1 or 2 in a pharmaceutically effective amount.

* * * * *